United States Patent [19]

Foster

[11] Patent Number: 5,225,537
[45] Date of Patent: Jul. 6, 1993

[54] METHODS FOR PRODUCING HYBRID PHOSPHOLIPID-BINDING PROTEINS

[75] Inventor: Donald C. Foster, Seattle, Wash.

[73] Assignee: ZymoGenetics, Inc., Seattle, Wash.

[21] Appl. No.: 459,082

[22] Filed: Dec. 29, 1989

[51] Int. Cl.$^5$ .................. C07K 15/12; C12N 9/64
[52] U.S. Cl. ...................................... 530/380; 530/384; 530/350; 435/69.6; 435/69.7; 435/219
[58] Field of Search ............... 530/380, 384; 435/69.6, 435/69.7, 219, 226

[56] References Cited

U.S. PATENT DOCUMENTS 4,770,999  9/1988  Kaufman et al. ............. 435/68.6
4,775,624 10/1988  Bang et al. ................... 436/226
4,784,950 11/1988  Hagen et al. ................. 435/68.6

FOREIGN PATENT DOCUMENTS 8803926 6/1988 World Int. Prop. O.

OTHER PUBLICATIONS

Furic et al. 1988. Cell 53:505-518.
Nagai et al. 1987, Methods in Enzymology 153:461-481.
Haagsman et al. 1987, J. Biol. Chem. 262(2):13877-13880.
Pan and Price, "The propeptide of rat bone γ-carboxyglutamic acid protein shares homology with other vitamin K-dependent protein precursors", *Proc. Natl. Acad. Sci. USA* 82:6109-6113, 1985.
Marlar et al., "Mechanism of Action of Human Activated Protein C, a Thrombin-Dependent Anticoagulant Enzyme", *Blood* 59:1067-1072, 1982.
Kisiel, et al., "Proteolytic Activation of Protein C from Bovine Plasma", *Biochemistry* 15:4893-4900, 1976.
Sugo et al., "Protein C in Bovine Plasma after Warfarin Treatment", *J. Biol. Chem.* 260:10453-10457, 1985.
Rannels et al., "Vitamin K-dependent carboxylation of pulmonary surfactant-associated proteins", *Proc. Natl. Acad. Sci. USA* 84:5952-5956, 1987.
Ross et al., "Phospholipid Binding and Biophysical Activity of Pulmonary Surfactant-associated Protein (SAP)-35 and Its Non-collagenous COOH-terminal Domains", *J. Biol. Chem.* 261:14283-14291 (1986).
Busby et al., "Expression of active human factor IX in transfected cells," *Nature* 316:271-273, 1985.
Kaufman et al., "Expression, Purification, and Characterization of Recombinant γ-Carboxylated Factor IX Synthesized in Chinese Hamster Ovary," *J. Biol. Chem.* 261:9622-9628, 1986.
de la Salle et al., "Active γ-carboxylated human factor IX expressed using recombinant DNA techniques," *Nature* 316:268-270, 1985.
Jorgensen et al., "Expression of Completely γ-Carboxylated Recombinant Human Prothrombin," *J. Biol. Chem.* 262:6729-6734, 1987.
Jackson, "Calcium Ion Binding to γ-Carboxyglutamic Acid-Containing Proteins From the Blood Clotting System: What We Still Don't Understand," in *Current Advances in Vitamin K Research: A Steenbock Symposium*, Suttie (ed.), New York, N.Y., pp. 305-324, 1988.
Fung and MacGillivray, "Organization of the Genes Coding for the Vitamin K-Dependent Clotting Factors," in *Current Advances in Vitamin K Research: A Steenbock Symposium*, Suttie (ed.), New York, N.Y., pp. 143-151, 1988.

(List continued on next page.)

Primary Examiner—Robert A. Wax
Assistant Examiner—Keith C. Furman
Attorney, Agent, or Firm—Seed and Berry

[57] ABSTRACT

Methods are disclosed for producing hybrid phospholipid-binding proteins from eukaryotic cells. DNA constructs comprising a transcriptional promoter, at least one signal sequence and a hybrid phospholipid-binding protein coding sequence comprising at least one lipocortin lipid-binding domain joined to a gla-domainless, vitamin K-dependent protein and a transcriptional terminator are also disclosed.

5 Claims, 11 Drawing Sheets

OTHER PUBLICATIONS

Price et al., "Molecular cloning of matrix Gla protein: Implications for substrate recognition by the vitamin K–dependent γ-carboyxlase," *Proc. Natl. Acad. Sci. USA* 84:8335–8339, 1987.

Tait et al., "Placental Anticoagulant Proteins: Isolation and Comparative Characterization of Four Members of the Lipocortin Family," *Biochemistry* 27:6268–6276, 1988.

Funakoshi et al., "Primary Structure of Human Placental Anticoagulant Protein," *Biochemsitry* 26:8087–8092, 1987.

Glenney, Jr. et al., "Calpactins: Two Distinct Ca++-regulated Phospholipid- and Actin-binding Proteins Isolated from Lung and Placenta," *J. Cell Biol.* 104:503–511, 1987.

Kristensen et al., "Primary Structure of Bovine Calpactin I Heavy Chain (p36), a Major Cellular Substrate for Retroviral Protein-Tyrosine Kinases: Homology with the Human Phospholipase $A_2$ Inhibitor Lipocortin," *Biochemistry* 25:4497–4503, 1986.

Saris et al., "The cDNA Sequence for the Protein-Tyrosine Kinase Substrate p36 (Calpactin I Heavy Chain) Reveals a Multidomain Protein with Internal Repeats," *Cell* 46:201–212, 1986.

Schlaepfer et al., "Structural and functional characterization of endonexin II, a calcium- and phospholipid-binding protein," *Proc. Natl. Acad. Sci. USA* 84:6078–6082, 1987.

Wallner et al., "Cloning and expression of human lipocortin, a phospholipase $A_2$ inhibitor with potential anti-inflammatory activity," *Nature* 320:77–81, 1986.

Crompton et al., "Diversity in the Lipocortin/Calpactin Family," *Cell* 55:1–3, 1988.

Geisow, "Common domain structure of $Ca^{2+}$ and lipid-binding proteins," *FEBS Lett.* 203:99–103, 1986.

Geisow et al., "A consensus amino-acid sequence repeat in *Torpedo* and mammalian $Ca^{2+}$-dependent membrane-binding proteins," *Nature* 320:636–638, 1986.

Huang et al., "Two Human 35 kd Inhibitors of Phospholipase $A_2$ Are Related to Substrates of pp60$^{v-STC}$ and of the Epidermal Growth Factor Receptor/Kinase," *Cell* 46:191–199, 1986.

Pepinsky et al., "Purification and Partial Sequence Analysis of a 37-kDa Protein that Inhibits Phospholipase $A_2$ Activity from Rat Peritoneal Exudates," *J. Biol. Chem.* 261:4239–4246, 1986.

Pepinsky et al., "Five Distinct Calcium and Phospholipid Binding Proteins Share Homology with Lipocortin I," *J. Biol. Chem.* 263:10799–10811, 1988.

Kretsinger and Creutz, "Consensus in exocytosis," *Nature* 320:573, 1986.

Iwasaki et al., "Structure and Expression of cDNA for an Inhibitor of Blood Coagulation Isolated from Human Placenta: A New Lipocortin-Like Protein," *J. Biochem.* 102:1261–1273, 1987.

Foster and Davie, "Characterization of a cDNA coding for human protein C," *Proc. Natl. Acad. Sci. USA* 81:4766–4770, 1984.

Foster et al., "The nucleotide sequence of the gene for human protein C," *Proc. Natl. Acad. Sci. USA* 82:4673–4677, 1985.

Hagen et al., "Characterization of a cDNA coding for human factor VII," *Proc. Natl. Acad. Sci. USA* 83:2412–2416, 1986.

O'Hara et al., "Nucleotide sequence of the gene coding for human factor VII, a vitamin K-dependent protein participating in blood coagulation," *Proc. Natl. Acad. Sci. USA* 84:5158–5162, 1987.

Kurachi and Davie, "Isolation and characterization of a cDNA coding for human factor IX," *Proc. Natl. Acad. Sci. USA* 79:6461–6464, 1982.

Anson et al., "The gene structure of human anti-haemophilic factor IX," *EMBO J.* 3:1053–1060, 1984.

Leytus et al., "Characterization of a cDNA coding for human factor X," *Proc. Natl. Acad. Sci. USA* 81:3699–3702, 1984.

Leytus et al., "Gene for Human Factor X: A Blood Coagulation Factor Whose Gene Organization Is Essentially Identical with That of Factor IX and Protein C," *Biochemistry* 25:5098–5102, 1986.

Lundwall et al., "Isolation and sequence of the cDNA for human protein S, a regulator of blood coagulation," *Proc. Natl. Acad. Sci. USA* 83:6716–6720, 1986.

Hoskins et al., "Cloning and characterization of human liver cDNA encoding a protein S precursor," *Proc. Natl. Acad. Sci. USA* 84:349–353, 1987.

(List continued on next page.)

OTHER PUBLICATIONS

Degen et al., "Characterization of the Complementary Deoxyribonucleic Acid and Gene Coding for Human Prothrombin," *Biochemistry* 22:2087–2097, 1983.

Kurachi et al., "Cloning and sequence of cDNA coding for $\alpha_1$-antitrypsin," *Proc. Natl. Acad. Sci. USA* 78:6826–6830, 1981.

Tone et al., "Structure of Human $\alpha_2$-Plasmin Inhibitor Deduced from the cDNA Sequence," *J. Biochem. (Tokyo)* 102:1033–1041, 1987.

Watson, "Compilation of published signal sequences," *Nuc. Acids Res.* 12:5145–5164, 1984.

Pennica et al., "Cloning and expression of human tissue-type plasminogen activator cDNA in *E. coli*," *Nature* 301:214–221, 1983.

von Heijne, "Patterns of Amino Acids near Signal-Sequence Cleavage Sites," *Eur. J. Biochem.* 133:17–21, 1983.

von Heijne, "How Signal Sequences Maintain Cleavage Specificity," *J. Mol. Biol.* 173:243–251, 1984.

von Heijne, "A new method for predicting signal sequence cleavage sites," *Nuc. Acids Res.* 14:4683–4690, 1986.

```
GGCTGTCATG GCGGCAGGAC GGCGAACTTG CAGTATCTCC ACGACCCGCC CCTGTGCCAG TGCCTCCAG
```

```
-42        -40                                     -30
ATG TGG CAG CTC ACA AGC CTC CTG CTG TTC GTG GCC ACC TGG GGA ATT TCC GGC
MET Trp Gln Leu Thr Ser Leu Leu Leu Phe Val Ala Thr Trp Gly Ile Ser Gly

-20                                     -10
ACA CCA GCT CCT CTT GAC TCA GTG TTC TCC AGC AGC GAG CGT GCC CAC CAG GTG
Thr Pro Ala Pro Leu Asp Ser Val Phe Ser Ser Ser Glu Arg Ala His Gln Val

-1  +1                         10
CTG CGG ATC CGC AAA CGT GCC AAC TCC TTC CTG GAG GAG CTC CGT CAC AGC AGC
Leu Arg Ile Arg Lys Arg Ala Asn Ser Phe Leu Glu Glu Leu Arg His Ser Ser 20                                     30
CTG GAG CGG GAG TGC ATA GAG GAG ATC TGT GAC TTC GAG GAG GCC AAG GAA ATT
Leu Glu Arg Glu Cys Ile Glu Glu Ile Cys Asp Phe Glu Glu Ala Lys Glu Ile

40
TTC CAA AAT GTG GAT GAC ACA CTG GCC TTC TGG TCC AAG CAC GTC GAC GGT GAC
Phe Gln Asn Val Asp Asp Thr Leu Ala Phe Trp Ser Lys His Val Asp Gly Asp 50                                  60
CAG TGC TTG GTC TTG CCC TTG GAG CAC CCG TGC GCC AGC CTG TGC TGC GGG CAC
Gln Cys Leu Val Leu Pro Leu Glu His Pro Cys Ala Ser Leu Cys Cys Gly His 70                                          80
GGC ACG TGC ATC GAC GGC ATC GGC AGC TTC AGC TGC GAC TGC CGC AGC GGC TGG
Gly Thr Cys Ile Asp Gly Ile Gly Ser Phe Ser Cys Asp Cys Arg Ser Gly Trp 90                                      100
GAG GGC CGC TTC TGC CAG CGC GAG GTG AGC TTC CTC AAT TGC TCG CTG GAC AAC
Glu Gly Arg Phe Cys Gln Arg Glu Val Ser Phe Leu Asn Cys Ser Leu Asp Asn 110                                  120
GGC GGC TGC ACG CAT TAC TGC CTA GAG GAG GTG GGC TGG CGG CGC TGT AGC TGT
Gly Gly Cys Thr His Tyr Cys Leu Glu Glu Val Gly Trp Arg Arg Cys Ser Cys

130
GCG CCT GGC TAC AAG CTG GGG GAC GAC CTC CTG CAG TGT CAC CCC GCA GTG AAG
Ala Pro Gly Tyr Lys Leu Gly Asp Asp Leu Leu Gln Cys His Pro Ala Val Lys 140                                 150
TTC CCT TGT GGG AGG CCC TGG AAG CGG ATG GAG AAG AAG CGC AGT CAC CTG AAA
Phe Pro Cys Gly Arg Pro Trp Lys Arg Met Glu Lys Lys Arg Ser His Leu Lys

160                             ↓170
CGA GAC ACA GAA GAC CAA GAA GAC CAA GTA GAT CCG CGG CTC ATT GAT GGG AAG
Arg Asp Thr Glu Asp Gln Glu Asp Gln Val Asp Pro Arg Leu Ile Asp Gly Lys
```

FIG. 2A

```
                    180                                           190
ATG ACC AGG CGG GGA GAC AGC CCC TGG CAG GTG GTC CTG CTG GAC TCA AAG AAG
Met Thr Arg Arg Gly Asp Ser Pro Trp Gln Val Val Leu Leu Asp Ser Lys Lys 200                                           210
AAG CTG GCC TGC GGG GCA GTG CTC ATC CAC CCC TCC TGG GTG CTG ACA GCG GCC
Lys Leu Ala Cys Gly Ala Val Leu Ile His Pro Ser Trp Val Leu Thr Ala Ala

220
CAC TGC ATG GAT GAG TCC AAG AAG CTC CTT GTC AGG CTT GGA GAG TAT GAC CTG
His Cys Met Asp Glu Ser Lys Lys Leu Leu Val Arg Leu Gly Glu Tyr Asp Leu 230                                     240
CGG CGC TGG GAG AAG TGG GAG CTG GAC CTG GAC ATC AAG GAG GTC TTC GTC CAC
Arg Arg Trp Glu Lys Trp Glu Leu Asp Leu Asp Ile Lys Glu Val Phe Val His 250                                     260
CCC AAC TAC AGC AAG AGC ACC ACC GAC AAT GAC ATC GCA CTG CTC CAC CTG GCC
Pro Asn Tyr Ser Lys Ser Thr Thr Asp Asn Asp Ile Ala Leu Leu His Leu Ala 270                                     280
CAG CCC GCC ACC CTC TCG CAG ACC ATA GTG CCC ATC TGC CTC CCG GAC AGC GGC
Gln Pro Ala Thr Leu Ser Gln Thr Ile Val Pro Ile Cys Leu Pro Asp Ser Gly 290                                     300
CTT GCA GAG CGC GAG CTC AAT CAG GCC GGC CAG GAG ACC CTC GTG ACG GGC TGG
Leu Ala Glu Arg Glu Leu Asn Gln Ala Gly Gln Glu Thr Leu Val Thr Gly Trp

310
GGC TAC CAC AGC AGC CGA GAG AAG GAG GCC AAG AGA AAC CGC ACC TTC GTC CTC
Gly Tyr His Ser Ser Arg Glu Lys Glu Ala Lys Arg Asn Arg Thr Phe Val Leu 320                                     330
AAC TTC ATC AAG ATT CCC GTG GTC CCG CAC AAT GAG TGC AGC GAG GTC ATG AGC
Asn Phe Ile Lys Ile Pro Val Val Pro His Asn Glu Cys Ser Glu Val Met Ser 340                                     350
AAC ATG GTG TCT GAG AAC ATG CTG TGT GCG GGC ATC CTC GGG GAC CGG CAG GAT
Asn Met Val Ser Glu Asn Met Leu Cys Ala Gly Ile Leu Gly Asp Arg Gln Asp 360                                     370
GCC TGC GAG GGC GAC AGT GGG GGG CCC ATG GTC GCC TCC TTC CAC GGC ACC TGG
Ala Cys Glu Gly Asp Ser Gly Gly Pro Met Val Ala Ser Phe His Gly Thr Trp 380                                     390
TTC CTG GTG GGC CTG GTG AGC TGG GGT GAG GGC TGT GGG CTC CTT CAC AAC TAC
Phe Leu Val Gly Leu Val Ser Trp Gly Glu Gly Cys Gly Leu Leu His Asn Tyr

400
GGC GTT TAC ACC AAA GTC AGC CGC TAC CTC GAC TGG ATC CAT GGG CAC ATC AGA
Gly Val Tyr Thr Lys Val Ser Arg Tyr Leu Asp Trp Ile His Gly His Ile Arg
```

*FIG. 2B*

```
   410                              419
GAC AAG GAA GCC CCC CAG AAG AGC TGG GCA CCT TAG CGACCCTCCC TGCAGGGCTG
Asp Lys Glu Ala Pro Gln Lys Ser Trp Ala Pro

GGCTTTTGCA TGGCAATGGA TGGGACATTA AAGGGACATG TAACAAGCAC ACCGGCCTGC TGTTCTGTCC

TTCCATCCCT CTTTTGGGCT CTTCTGGAGG GAAGTAACAT TTACTGAGCA CCTGTTGTAT GTCACATGCC

TTATGAATAG AATCTTAACT CCTAGAGCAA CTCTGTGGGG TGGGGAGGAG CAGATCCAAG TTTTGCGGGG

TCTAAAGCTG TGTGTGTTGA GGGGGATACT CTGTTTATGA AAAGAATAA AAAACACAAC CACGAAAAAA
```

FIG. 2C

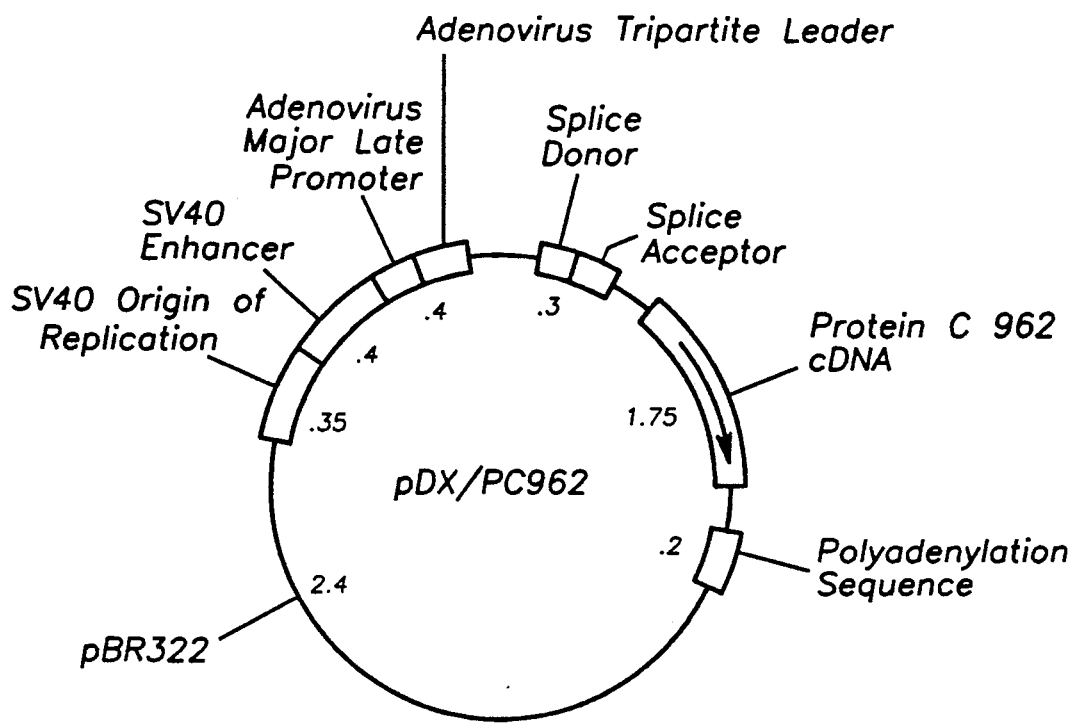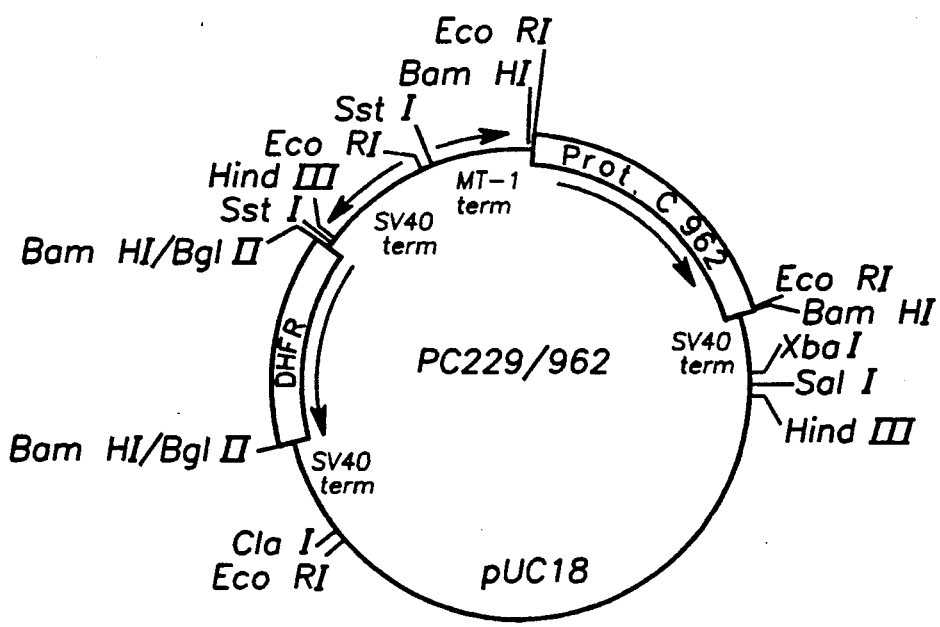
FIG. 6

FIG. 7

METHODS FOR PRODUCING HYBRID PHOSPHOLIPID-BINDING PROTEINS

DESCRIPTION

1. Technical Field

The present invention relates to the production of proteins in general, and more specifically, to the production of hybrid phospholipid-binding proteins and to DNA sequences encoding these proteins.

2. Background of the Invention

Vitamin K is a cofactor of the microsomal enzymes that perform post-translational conversion of glutamyl residues (glu) to γ-carboxyglutamyl residues (gla) in domains of certain proteins. These proteins, termed vitamin K-dependent proteins, contain domains that have been identified to contain gla residues, termed gla domains. The γ-carboxylation of glu residues in the gla domains of vitamin K-dependent proteins is required for the biological function of these proteins. The gla residues bind calcium ions and are believed to be responsible for the interaction between vitamin K-dependent proteins and phospholipids, which is required for the biological activity of such proteins.

Vitamin K-dependent proteins, which include prothrombin, factor VII, factor IX, factor X, protein C, protein S, bone gla protein, bone matrix protein, protein Z and pulmonary surfactant-associated proteins, play roles in the regulation and promotion of blood coagulation, skeletal growth and lung development. Prothrombin, factor VII, factor IX, and factor X, for example, play important roles in clot formation. The formation of a fibrin clot is the result of a "cascade" of protein activations that involves a number of blood proteins. These proteins, termed "coagulation factors," are generally proenzymes or zymogens, enzymatically inactive proteins that are converted to proteolytic enzymes by the action of an activator, itself an activated clotting factor. Coagulation factors which have undergone such conversion are generally referred to as "activated factors," and are designated by the addition of a lower case "a" (e.g., VIIa). Activation of proenzyme forms is generally accelerated in the presence of acidic phospholipids and $Ca^{2+}$ ions. It is believed that in the presence of $Ca^{2+}$ ions the activating enzyme and proenzyme form a complex with each other and with acidic phospholipids in the cell membrane (for review, see Jackson and Nemerson, *Ann. Rev. Biochem.* 49:765-811, 1980).

Protein C, for example, plays a role in the regulation of coagulation through inactivation of factor Va and factor VIIIa by limited proteolysis in the presence of phospholipid and calcium ions. Protein S acts as a cofactor to activated protein C to facilitate the activated protein C-catalyzed proteolysis of factor Va (Walker, *J. Biol. Chem.* 255:5521-5524, 1980).

Several Vitamin K-dependent proteins are used therapeutically. Factors VII, IX and X are used as therapeutics to promote blood coagulation in individuals who lack sufficient levels of these coagulation proteins. Therapeutic uses of factor VII exist in the treatment of individuals exhibiting a deficiency in factor VII, as well as factor VIII and factor IX deficient populations, and individuals with Von Willebrand's disease. Recent studies have indicated that small amounts (40-50 micrograms) of injected factor VIIa are effective in controlling serious on-going bleeding episodes in factor VIII-deficient patients who have high levels of anti-factor VIII antibodies in their blood (Hedner and Kisiel, *J. Clin. Invest.* 71:1836-1841, 1983). Protein C may be used as a therapeutic to treat thrombotic disorders in protein C-deficient individuals.

Current methods for producing vitamin K-dependent proteins are limited to expression from cultured mammalian cells and isolation from biological fluids. Isolation of vitamin K-dependent proteins from biological fluids is costly due to the availability of the starting materials and the manipulations required for purification of the proteins. Protein C, for example, is a trace plasma protein and the purification of protein C from plasma in commercial quantities remains difficult. Current purification methods depend on the purification of vitamin K-dependent proteins from cryoprecipitates from diverse sources of plasma. As such there is the additional risk of co-purifying infective agents such as hepatitis virus, HTLV III and HTLV I.

Recombinant vitamin K-dependent proteins may be expressed from cultured mammalian cells. While high levels of some recombinant vitamin K-dependent proteins may be isolated from cultured mammalian cells, only a small percentage of the proteins are biologically active. Kaufman et al. (*J. Biol. Chem.* 261:9622-9628, 1986) have reported secretion of recombinant factor IX from Chinese hamster ovary cells at levels of 180 μg/ml, but only 1.5 μg/ml of the material is biologically active. Busby et al. (*Nature* 316:271-273, 1985) reported the expression of recombinant factor IX with only 50% biological activity. De la Salle (*Nature* 316:268-270, 1985) reported that recombinant factor IX expressed from mouse fibroblasts was not fully active. This lack of activity may be due to the inability of the host cells to properly process (e.g., gamma carboxylate) the protein.

There is therefore a need in the art for a method of producing relatively large amounts of pure preparations of proteins having substantially the same biological activity as vitamin K-dependent proteins. The present invention fulfills this need through the use of recombinant DNA technology, eliminating the problems of viral contamination and low expression of biologically active recombinant proteins.

DISCLOSURE OF INVENTION

Briefly stated, the present invention provides DNA sequences that code for biologically active hybrid phospholipid-binding proteins. In one aspect of the invention a DNA sequence encoding a hybrid phospholipid-binding protein comprises at least one lipocortin phospholipid-binding domain joined to a gla-domainless, vitamin K-dependent protein. Preferably, the phospholipid-binding domain is a phospholipid-binding domain of a protein selected from the group consisting of lipocortin I, lipocortin II, lipocortin III, lipocortin IV, PAP-I, lipocortin VI, and PAP-III. Preferred gla-domainless, vitamin K-dependent proteins include the gla-domainless portions of proteins selected from the group consisting of factor VII, factor IX, factor X, protein C, protein S, bone gla protein, bone matrix protein, protein, Z and pulmonary surfactant-associated proteins.

In addition, the invention discloses DNA constructs capable of directing the expression of hybrid phospholipid-binding proteins. The DNA constructs comprise the following operably linked elements: a transcriptional promoter, at least one secretory signal sequence, a DNA sequence encoding a hybrid phospholipid-binding protein comprising at least one lipocortin phospholipid-binding domain joined to a gla-domainless vitamin K-dependent protein and a transcriptional terminator.

A third aspect of the invention discloses cultured eukaryotic cells transfected to produce hybrid phospholipid-binding proteins The cells contain a DNA construct comprising the following operably linked elements: a transcriptional promoter, at least one secretory signal sequence, a DNA sequence encoding a hybrid phospholipid-binding protein comprising at least one lipocortin phospholipid-binding domain joined to a gla-domainless vitamin K-dependent protein and a transcriptional terminator.

In a further aspect of the invention, methods are disclosed for producing hybrid phospholipid-binding proteins. The methods comprise the steps of (a) introducing into a cultured eukaryotic cell an expression vector containing a DNA construct comprising the following operatively linked elements: a transcriptional promoter, at least one secretory signal sequence, a DNA sequence encoding a hybrid phospholipid-binding protein comprising at least one lipocortin phospholipid-binding domain joined to a gla-domainless vitamin K-dependent protein and a transcriptional terminator, (b) culturing the eukaryotic cell to produce the protein encoded by the DNA construct, and (c) isolating the protein encoded by the DNA construct and produced by the cells.

In yet another aspect of the invention, hybrid phospholipid-binding proteins produced from cells containing a DNA construct comprising the following operatively linked elements: a transcriptional promoter, at least one secretory signal sequence, a DNA sequence encoding a hybrid phospholipid-binding protein comprising at least one lipocortin phospholipid-binding domain joined to a gla-domainless vitamin K-dependent protein and a transcriptional terminator are disclosed. In one embodiment, the hybrid phospholipid-binding protein comprises at least one phospholipid-binding domain joined to gla-domainless protein C.

BRIEF DESCRIPTION OF THE DRAWINGS

FIG. 2A, 2B and 2C illustrate the nucleotide sequence of
the complete protein C cDNA and the deduced amino acid sequence of protein C The arrow indicates the cleavage site between the activation peptide and the heavy chain.

FIG. 6 illustrates the expression vectors pDX/PC962 and PC229/962.

FIG. 7 shows the cDNA sequence encoding PAP-I and the amino acid sequence deduced from the cDNA sequence.

BEST MODE FOR CARRYING OUT THE INVENTION

Figure 1:
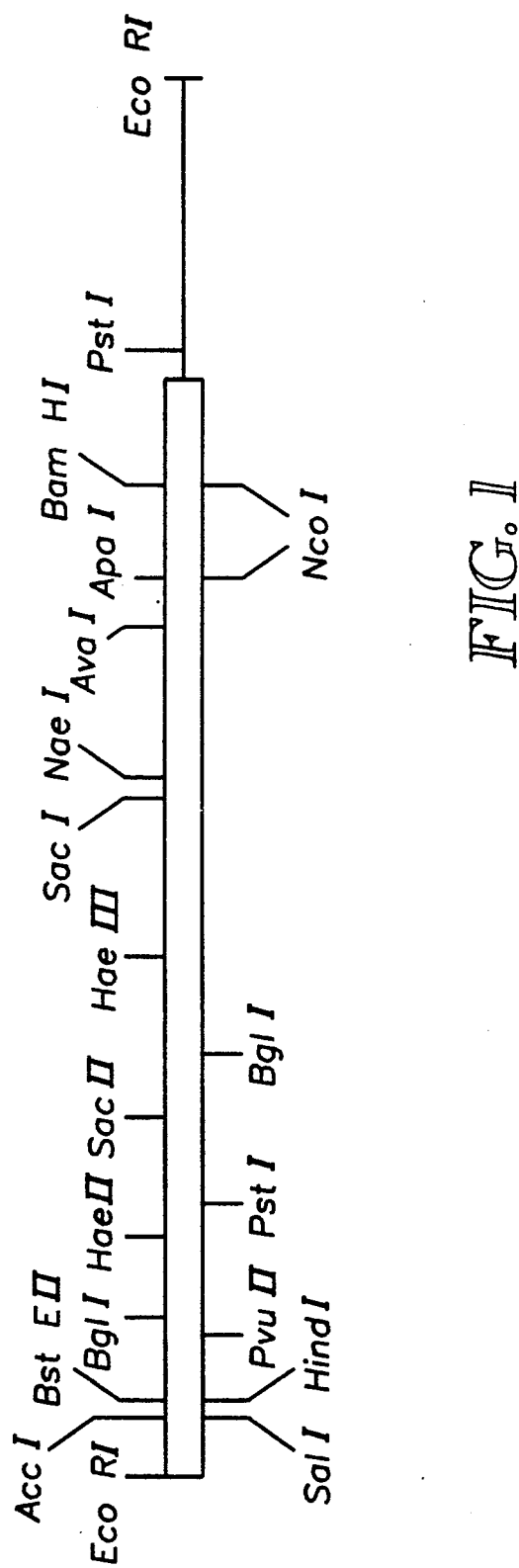
FIG. 1 is a partial restriction map of the protein C cDNA in pHCλ6L. The coding region is indicated by an open box.

Prior to setting forth the invention, it may be helpful to an understanding thereof to set forth definitions of certain terms to be used hereinafter.

Phospholipid: Phospholipids are a class of compounds consisting of fatty acid molecules esterified to the first and second hydroxyl groups of glycerol, with the third hydroxyl group of the glycerol moiety esterified to phosphoric acid. Phospholipids occur in cell membranes and, as noted above, contribute to blood coagulation. For example, prothrombin and factor Xa bind to membrane phospholipids in the presence of calcium, resulting in the activation of prothrombin to thrombin.

Secretory Signal Sequence: A DNA sequence encoding a secretory peptide. A secretory peptide, sometimes referred to as a pre peptide, is an amino acid sequence that acts to direct the secretion of a mature polypeptide or protein from a cell. Secretory peptides are characterized by a core of hydrophobic amino acids and are typically, but not exclusively, found at the amino termini of newly synthesized proteins. Very often the secretory peptide is cleaved from a mature protein during secretion. Processing sites may occur naturally within a secretory peptide or may be added to a secretory peptide by, for example, in vitro mutagenesis. Certain secretory peptides may be used in concert to direct the secretion of polypeptides and proteins. One such secretory peptide that may be used in combination with other secretory peptides is the third domain of the yeast protein Barrier. As used herein, the term "secretory peptide" may also mean a functional portion of a naturally occurring secretory peptide.

Gla Domain: An amino acid sequence generally containing from about 26 to about 45 amino acids, generally but not always located in the amino terminal region of a protein, that contains between three and twelve glutamyl residues that are post-translationally modified to γ-carboxyglutamyl residues (gla). In some cases, the gla domain may be defined by exon-intron boundaries of the genomic sequence. Protein C, for example, has a gla domain that is encoded within Exon II of the genomic sequence. Gla-domains, which facilitate the calcium-mediated binding of vitamin K-dependent proteins and membrane phospholipids, are required for the biological activity of vitamin K-dependent proteins As used herein, gla-domainless vitamin K-dependent proteins are understood to lack a functional gla domain such that the resultant protein is biologically inactive and fails to bind to phospholipids.

DNA Construct: A DNA molecule, or a clone of such a molecule, either single or double-stranded, which has been modified through human intervention to contain segments of DNA combined and juxtaposed in a manner that would not otherwise exist in nature.

Joined: Two or more DNA coding sequences are said to be joined when, as a result of in-frame fusions between the DNA coding sequences or as a result of the removal of intervening sequences by normal cellular processing, the DNA coding sequences can be translated into a polypeptide.

Expression Vector: A DNA molecule which contains, inter alia, a DNA sequence encoding a protein of interest together with a promoter and other sequences that facilitate expression of the protein. Expression vectors further contain genetic information that provides for their replication in a host cell, either by autonomous replication or by integration into the host genome. Examples of expression vectors commonly used for recombinant DNA are plasmids and certain viruses, although they may contain elements of both. They also may include a selectable marker.

Biological Activity: A function or set of functions performed by a molecule in a biological context (i.e., in an organism or an in vitro facsimile thereof). Biological activities of proteins may be divided into catalytic and effector activities. Catalytic activities of vitamin K-dependent plasma proteins, for example, generally involve specific proteolytic cleavages of other plasma proteins, resulting in activation or deactivation of the substrates. Effector activities include specific binding of the biologically active molecules to phospholipids or other small molecules, to macromolecules, such as proteins, or to cells. Effector activity frequently augments, or is essential to, catalytic activity under physiological conditions.

For example, the biological activity of activated protein C is characterized by its anticoagulant and fibrinolytic properties. Activated protein C inactivates factor Va and factor VIIIa in the presence of acidic phospholipids and calcium. Protein S appears to be involved in the regulation of this function (Walker, *J. Biol. Chem.* 255:5521–5524, 1980).

As noted above, vitamin K-dependent proteins require the vitamin K-dependent post-translational γ-carboxylation of specific glutamyl residues in their gla domains for biological activity. The resultant γ-carboxyglutamyl residues in the gla domain are required for calcium-mediated binding to phospholipid.

Vitamin K-dependent proteins such as prothrombin, factor VII, factor IX, factor X, protein C, protein Z, bone gla protein and protein S show both structural and sequence homology in the pro-peptide region, the putative targeting signal for the γ-carboxylase, and in the amino-terminal region of the light chain. Vitamin K-dependent proteins show significant homology in the propeptide region from -1 to -17 and in the first 45 amino acids of the mature coding sequence of the light chain, including a distinctive conservation in post-translationally modified glu residues (for review, see Jackson, in *Current Advances in Vitamin K Research*, Suttie (ed.), Elsevier Science Publishing Co., New York, N.Y., 1988, pp. 305–324). Matrix gla protein shows a significant homology with the pro-peptide regions and gla domains of vitamin K-dependent plasma proteins and bone gla protein (Price et al., *Proc. Natl. Acad. Sci. USA* 84:8335–8339, 1987).

Vitamin K-independent, phospholipid-binding proteins have been reported in the literature. These proteins include lipocortins (for review, see Pepinsky et al., *J. Biol. Chem.* 263:10799–10811, 1988), "E-F hand" calcium-binding proteins, phospholipase $A_2$ and protein kinase C. Lipocortins (also known as macrocortin, lipomodulin and renocortin), for example, are a group of intracellular proteins that share several properties including the inhibition of phospholipase $A_2$ and calcium-dependent phospholipid binding. As inhibitors of phospholipase $A_2$, lipocortins have been implicated in the regulation of inflammation. However, the true physiological role of lipocortins has not been elucidated. Lipocortins have been detected in a variety of cell types and tissues and share common structural features. These proteins have been reported to have an apparent mass of approximately 40 kDa and generally contain four internal repeats. It is believed that the calcium binding and phospholipid-binding domains occur in each of these repeats. The four phospholipid-binding domains of lipocortins are generally from 70 to 80 amino acids in length and contain a 17 amino acid consensus sequence. The consensus sequence is defined herein as significantly statistically related, as defined by Dayhoff (M. O. Dayhoff (ed.), *Atlas of Protein Sequence and Structure*, National Biomedical Research Foundation, Washington, D.C., 1979, Vol. 5, Suppl. 3, pp. 1–8) or identical to the sequence Lys-Gly-1-Gly-Thr-2-3-4-5-Leu-6-Arg-7-8-Val-Ser-Arg, wherein 1 is usually a hydrophobic residue, 2 is Arg or Asp or is a related amino acid, as defined by Dayhoff (ibid.), 3 is Met, Asp, Gln or is a related amino acid, as defined by Dayhoff (ibid.), 4 is Lys, Phe, Asn, Met or is a related amino acid, as defined by Dayhoff (ibid.), 5 is Ala, Thr or Val, 6 is Ile or Asn, 7 is Met or Ile, and 8 is Ser or Ala. Table 1 shows the current nomenclature for lipocortins (Pepinsky et al., *J. Biol. Chem.* 263:10799–10811, 1988; Tait et al., *Biochemistry* 27:6268–6276, 1988).

TABLE 1

| | |
|---|---|
| Lipocortin I | p35 |
| | Chromobindin - 9 |
| | Calpactin II |
| Lipocortin II | p36 |
| | Chromobindin - 8 |
| | Calpactin I |
| | Protein I |
| | PAP-IV |
| Lipocortins III and IV | Endonexin |
| | Chromobindin - 4 |
| | 35 kDa - Calcimedin |
| | p32.5 Calelectrin |
| | Protein II |
| Lipocortin V | Renocortin |
| | Chromobindin - 5 |
| | Endonexin - II |
| | Placental Anticoagulant Protein-I (PAP-I) |
| Lipocortin VI | Protein III |
| | p68 |
| | Chromobindin - 20 |
| | 67 kDa - Calcimedin |
| | 67 kDa - Calelectrin |
| PAP III | |

The present invention provides novel proteins that have substantially the same biological activity as vitamin K-dependent proteins or activated vitamin K-dependent proteins. These novel proteins, termed hybrid phospholipid-binding proteins, are hybrid proteins resulting from fusions between at least one phospholipid-binding domain of a lipocortin and a gla-domainless vitamin K-dependent protein. The proteins of the present invention also include variants and analogs of such proteins, as described below.

Suitable phospholipid-binding domains may be isolated from any one of the lipocortins shown in Table 1, the coding sequences of which have been reported in the literature. As used herein, a lipocortin phospholipid-binding domain is understood to contain a sequence of amino acids capable of binding to phospholipids in a calcium-dependent manner and contains the previously noted 17 amino acid consensus sequence. A particularly preferred lipocortin is placental anticoagulant protein-I, hereinafter referred to as PAP-I (Funakoshi et al., *Biochemistry* 26:8087-8092, 1987) (PAP-I is also known as lipocortin V).

Complementary DNA sequences for lipocortins I, II and III have been described (Saris et al., *Cell* 46:201-212, 1986; Huang et al., *Cell* 46:191-199, 1986 and Pepinsky et al., *J. Biol. Chem.* 263:10799-10811, 1988, respectively). The DNA sequence for PAP-I has been described Funakoshi et al. (*Biochemistry* 26:8087-8092, 1987; and in pending U.S. patent application Ser. No. 152,383, which is incorporated herein by reference).

Suitable gla-domainless vitamin K-dependent proteins may be generated from genomic DNA or cDNA sequences by deleting DNA sequences encoding gla domains from DNA sequences encoding vitamin K-dependent proteins, which include prothrombin, factor VII, factor IX, factor X, protein C, protein S, bone gla protein, bone matrix protein, protein Z, pulmonary surfactant-associated proteins, including variants thereof. DNA sequences encoding the gla domains of the above-mentioned proteins have been reported in the literature (for review, see Jackson, ibid.). The gla domain DNA sequences may be removed by loop-out mutagenesis, may be removed by restriction enzyme digestion and exonuclease digestion. DNA sequences encoding gla-domainless vitamin-K dependent proteins, such as those mentioned above, may be synthesized using standard laboratory techniques. Alternatively, a DNA sequence encoding a lipocortin phospholipid-binding domain joined to a vitamin K-dependent protein may be modified using conventional techniques to remove the sequences encoding the gla domain. Cloned DNA sequences encoding, for example, protein C (Foster and Davie, *Proc. Natl. Acad. Sci. USA* 81:4766-4770, 1984; Foster et al., *Proc. Natl. Acad. Sci. USA* 82:4673-4677, 1985; and Bang et al., U.S. Pat. No. 4,775,624), factor VII (Hagen et al., *Proc. Natl. Acad. Sci. USA* 83:2412-2416, 1986), factor IX (Kurachi and Davie, *Proc. Natl. Acad. Sci. USA* 79:6461-6464, 1982), and factor X (Leytus et al., *Proc. Natl. Acad. Sci. USA* 81:3699-3702, 1984) have been described. The gla domain for protein C, extending from amino acid 1 of the mature form of protein C to amino acid 45, has been identified by homology with other vitamin K-dependent proteins.

In general, cDNA sequences are preferred for carrying out the present invention due to their lack of intervening sequences which can lead to aberrant RNA processing and reduced expression levels. Complementary DNAs encoding protein C, for example, may be obtained from libraries prepared from liver cells according to standard laboratory procedures. It will be understood however, that suitable DNA sequences can also be obtained from genomic clones or can be synthesized de novo according to conventional procedures. If partial clones are obtained, it is necessary to join them in proper reading frame to produce a full length clone, using such techniques as endonuclease cleavage, ligation, and loop-out mutagenesis.

The coding sequences for the lipocortin phospholipid-binding domain(s) and the gla-domainless vitamin K-dependent protein are joined to produce a hybrid phospholipid-binding protein. Conventional procedures of endonuclease cleavage, exonuclease digestion, ligation and in vitro mutagenesis may be used to achieve the proper fusion. For example, DNA sequences encoding a phospholipid-binding domain and the gla-domainless vitamin K-dependent protein can be joined at a convenient restriction site followed by loop-out mutagenesis to precisely remove the gla domain sequence and directly join the phospholipid-binding domain with the gla-domainless vitamin K-dependent protein coding sequence. Alternatively, a lipocortin DNA sequence may be joined to a gla-domainless vitamin K-dependent protein by restriction enzyme digestion, synthetic adapter addition, or in vitro mutagenesis to directly joint the lipocortin coding sequence to the gla-domainless vitamin K-dependent protein coding sequence.

To direct proteins of the present invention into the secretory pathway of the host cell, at least one secretory signal sequence is used in conjunction with the DNA sequence of interest. Secretory signals include the factor VII signal sequence (Hagen et al., *Proc. Natl. Acad. Sci. USA* 83:2413-2416, 1986), the factor IX signal sequence (Kurachi and Davie, *Proc. Natl. Acad. Sci. USA* 79:646 464, 1982), the factor X signal sequence (Leytus et al., *Biochemistry* 25:5098-5102, 1986), the protein S signal sequence (Lundwall et al., *Proc. Natl. Acad. Sci. USA* 83:6716-6720, 1986), and the prothrombin signal sequence (Degen et al., *Biochemistry* 22:2087-2097, 1983). Particularly preferred signal sequences are the α-1-antitrypsin signal sequence (Kurachi et al., *Proc. Natl. Acad. Sci. USA* 78:6826-6830, 1981), the protein C signal sequence (Foster et al,. *Proc. Natl. Acad. Sci. USA* 82:4673-4677, 1985), and the α-2 plasmin inhibitor signal sequence (Tone et al., *J. Biochem.* (Tokyo) 102:1033-1042, 1987). A particularly preferred signal sequence is the tissue plasminogen activator signal sequence (Pennica et al., *Nature* 301:214-221, 1983). Alternatively, a secretory signal sequence may be synthesized according to the rules established, for example, by von Heinje (*Eur. J. Biochem.* 133:17-21, 1983; *J. Mol. Biol.* 184:99-105, 1985; *Nuc. Acids. Res.* 14:4683-4690, 1986).

Secretory signal sequences may be used singly or in combination. For example, a secretory signal sequence may be combined with a sequence encoding the third domain of the yeast Barrier protein (described in EP 310,137, which is incorporated by reference herein in its entirety). The sequence encoding the third domain of Barrier may be positioned in proper reading frame 3' of the DNA sequence of interest or 5' to the DNA sequence of interest and in proper reading frame with both the secretory signal sequence and the DNA sequence of interest.

Eukaryotic cells are preferred as host cells within the present invention. Exemplary eukaryotic host cells are cultured mammalian cells. Preferred cultured mammalian cells for use in the present invention include the COS-1 (ATCC CRL 1650), BHK, and 293 (ATCC CRL 1573; Graham et al., *J. Gen. Virol.* 36:59-72, 1977) cell lines. A preferred BHK cell line is the tk⁻ts13 BHK cell line (Waechter and Baserga, *Proc. Natl. Acad. Sci. USA* 79:1106-1110, 1982). A tk⁻ BHK cell line is available from the American Type Culture Collection, Rockville, Md., under accession number CRL 1632. In addition, a number of other mammalian cell lines may be used within the present invention, including Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CC 29.1), NCTC 1469 (ATCC CCL 9.1) and DUKX cells (Urlaub and Chasin, *Proc. Natl. Acad. Sci USA* 77:4216–4220, 1980).

Expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41:521–530, 1985) and the SV40 promoter (Subramani et al., *Mol. Cell. Biol.* 1:854–864, 1981). Cellular promoters include the mouse metallothionein-I promoter (Palmiter et al., *Science* 222:809–814, 1983), a mouse $V_\kappa$ promoter (Bergman et al., *Proc. Natl. Acad. Sci. USA* 81:7041–7045, 1983; Grant et al., *Nuc. Acids Res.* 15:5496, 1987) and a mouse $V_H$ promoter (Loh et al., *Cell* 33:85–93, 1983). A particularly preferred promoter is the major late promoter from Adenovirus 2 (Kaufman and Sharp, *Mol. Cell. Biol.* b 2:1304–13199, 1982). Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 EIB region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Vectors may also include enhancer sequences, such as the SV40 enhancer and the mouse $\mu$ enhancer (Gillies, *Cell* 33:717–728, 1983). Expression vectors may also include sequences encoding the adenovirus VA RNAs.

Variants of the vitamin K-dependent proteins for use in the present invention include those containing minor amino acid changes, such as those due to genetic polymorphisms, and those in which blocks of amino acids have been added, deleted or replaced without substantially altering the biological activity of the proteins. The processing of hybrid phospholipid-binding proteins requiring activation by proteolytic cleavage may be enhanced by modifying the cleavage site. A hybrid phospholipid-binding protein comprising gla-domainless protein C, for example, may be modified to enhance cleavage of the precursor to the two-chain form. Alternatively, a DNA sequence encoding protein C, for example, may be first modified to enhance the cleavage of the precursor and then joined with a lipocortin phospholipid-binding domain to construct a DNA sequence encoding a hybrid phospholipid-binding protein. Modified cleavage sites for protein C include amino acid sequences $(R_1)_n$-$R_2$-$R_3$-$R_4$, wherein $R_1$ through $R_4$ are lysine (Lys) or arginine (Arg) and n is an integer between 0 and 3 located between the light and heavy chains and $R_1$-$R_2$-$R_3$-$R_4$-X-$R_5$-$R_6$-$R_7$-$R_8$, wherein $R_1$ through $R_8$ are Lys or Arg and X is a peptide bond or a spacer peptide of 1 to 12 amino acids between the light and heavy chains (described in abandoned, commonly assigned U.S. patent applications Ser. Nos. 07/317,205; 130,370; and 144,357, which are incorporated by reference herein). Preferred spacer sequences include the amino acid sequences of Ala-Asn-Ser and Asn-Ile-Leu-Asn. As used herein, the light chain of protein C is understood to comprise amino acids 1–149 of the sequence disclosed in FIG. 1 or sequences substantially homologous thereto, or sequences with C-terminal extensions. The heavy chain of protein C may or may not include the activation peptide. The heavy chain of activated protein C is understood not to include the activation peptide. Processing may also be enhanced by modifying the host cell. Processing of protein C, for example, by cleavage after a dibasic dipeptide such as Arg-Lys (e.g., amino acids 156–157 of the native sequence) and subsequent removal of these amino acids may be enhanced by introducing the *S. cerevisiae* KEX1 and/or KEX2 genes into the host cell (described in abandoned, commonly assigned U.S. patent application Ser. Nos. 07/317,205; 130,370; and 144,357, which are incorporated herein by reference). The KEX2 gene encodes an endopeptidase that cleaves after a dibasic amino acid sequence (Fuller et al., in Leive (ed.), *Microbiology: 1986, 1986,* pp. 273–278); the expression of the KEX1 gene (Dmochowska et al., *Cell* 50:573–584, 1987) results in the subsequent removal of these dibasic amino acids. A cultured mammalian cell transfected with one or both of these genes is thus useful for expressing hybrid phospholipid-binding proteins having substantially the same activity as protein C or activated protein C.

Cloned DNA sequences may be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973.) Other techniques for introducing cloned DNA sequences into mammalian cells, such as electroporation (Neumann et al., *EMBO J.* 1:841–845, 1982), may also be used. In order to identify cells that have integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. A preferred amplifiable selectable marker is a gene encoding dihydrofolate reductase (DHFR). Selectable markers are reviewed by Thilly (*Mammalian Cell Technology*, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture that is introduced into the cells.

Transfected mammalian cells are allowed to grow for a period of time, typically 1–2 days, to begin expressing the DNA sequence(s) of interest Drug selection is then applied to select for growth of cells that are expressing the selectable marker in a stable fashion and to select for increased copy number of the cloned sequences, thereby increasing expression levels.

Host cells containing DNA constructs of the present invention are then cultured to produce the hybrid phospholipid-binding proteins of the present invention. The cells are cultured according to standard methods in a culture medium containing nutrients required for growth of cultured mammalian cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient, which are complemented by one or more selectable markers. Cultured mammalian cells are generally cultured in commercially available serum-containing or serum-free media. Selection of a medium appropriate for the particular cell line used is within the level of ordinary skill in the art.

The hybrid phospholipid-binding proteins produced according to the present invention may be isolated from cells transfected with DNA constructs comprising DNA sequences encoding such hybrid phospholipid-binding proteins. Isolation generally involves first separating the media from the cells and secondly purifying the proteins from the media. Purification methods include affinity chromatography, ion exchange chromatography, high-performance liquid chromatography and gel filtration. Purification by affinity chromotography on an antibody column using antibodies directed against either the phospholipid-binding domains or the gla-domainless vitamin K-dependent protein. Antibodies directed against the gla-domainless vitamin K-dependent protein or against the phospholipid-binding domains may be generated using conventional techniques. Monoclonal antibodies may be generated using methods well known in the literature and reviewed by, for example, Hurrell (*Monoclonal Hybridoma Antibodies: Techniques and Applications*, CRC Press, Inc., 1982). The isolation of hybrid phospholipid-binding proteins containing, for example, gla-domainless protein C can be purified by affinity chromatography using protein C-specific monoclonal antibodies. The hybrid phospholipid-binding protein may be eluted from the antibody column by elution with 6 M guanidine hydrochloride or with pH 11.5 buffer (25 mM potassium phosphate, pH 11.5, 0.2 M NaCl, 2% Tween-80, 0.5% $NaN_3$). Additional purification of the column eluate may be achieved by conventional chemical purification, such as by high-performance liquid chromatography (HPLC).

A hybrid phospholipid-binding protein encoding, for example, a gla-domainless protein C produced according to the present invention may be activated by removal of the activation peptide from the amino terminus of the heavy chain. Activation may be achieved by incubating the hybrid phospholipid-binding protein in vitro in the presence of α-thrombin (Kisiel, ibid., 1979), trypsin (Marlar et al., *Blood* 59:1067–1072, 1982), Russell's viper venom factor X activator (Kisiel et al., *Biochemistry* 15:4893–4900, 1976) or the commercially available venom-derived activator Protac C (American Diagnostica).

Alternatively, a hybrid phospholipid-binding protein encoding activated protein C or an activated protein C precursor may be activated in vivo by the action of endogenous proteases or by the action of a co-expressed KEX2 gene product. In vivo activation of protein C may be augmented by altering the cleavage sites between the light and heavy chains and/or between the heavy chain and the activation peptide.

Hybrid phospholipid-binding proteins of the present invention may be used in pharmaceutical compositions for topical or intravenous application. The protein will generally be used in combination with a physiologically acceptable carrier or diluent Preferred carriers and diluents include saline and sterile water. Pharmaceutical compositions may also contain stabilizers and adjuvants. The resulting aqueous solutions may be packaged for use or filtered under aseptic conditions and lyophilized, the lyophilized preparation being combined with a sterile aqueous solution prior to administration.

To summarize the examples which follow, Example 1 describes the cloning of DNA sequences encoding human protein C. Example 2 describes the construction of PC229/962. Example 3 describes the cloning of a cDNA encoding PAP-I. Example 4 describes the construction of a PAP-I-protein C fusion. Example 5 describes the expression of PAP-I-protein C in mammalian cells.

The following examples are offered by way of illustration and not by way of limitation.

EXAMPLES

Restriction endonucleases and other DNA modification enzymes (e.g., T4 polynucleotide kinase, calf alkaline phosphatase, DNA polymerase I (Klenow fragment), T4 polynucleotide ligase) were obtained from Boehringer Mannheim Biochemicals, Bethesda Research Laboratories (BRL) and New England Biolabs and were used as directed by the manufacturer, unless otherwise noted.

Oligonucleotides were synthesized on an Applied Biosystems Model 380A DNA synthesizer and purified by polyacrylamide gel electrophoresis on denaturing gels. *E. coli* cells were transformed as described by Maniatis et al. (*Molecular Cloning: A Laboratory Manual,* Cold Spring Harbor Laboratory, 1982). M13 and pUC cloning vectors and host strains were obtained from BRL.

EXAMPLE 1

Cloning of DNA Sequences Encoding Human Protein C

A cDNA coding for a portion of human protein C was prepared as described by Foster and Davie. Briefly, a λgt11 cDNA library was prepared from human liver mRNA by conventional methods. Clones were screened using an $^{125}$I-labeled affinity-purified antibody to human protein C, and phage were prepared from positive clones by the plate lysate method (Maniatis et al., ibid.), followed by banding on a cesium chloride gradient. The cDNA inserts were removed using Eco RI and were subcloned into plasmid pUC9 (Vieira and Messing, *Gene* 19:259–268, 1982). Restriction fragments were subcloned in the phage vectors M13mp10 and M13mp11 (Messing, *Meth. Enzymol.* 101:20–77, 1983) and were sequenced by the dideoxy method (Sanger et al., *Proc. Natl. Acad. Sci. USA* 74:5463–5467, 1977). A clone was selected that contained DNA corresponding to the known partial sequence of human protein C (Kisiel, ibid., 1979) and encoded protein C beginning at amino acid 64 of the light chain and extending through the heavy chain and into the 3' non-coding region. This clone was designated λHC1375. A second cDNA clone coding for protein C from amino acid 24 was also identified. The insert from the larger clone was subcloned into pUC9 and the plasmid was designated pHCλ6L (FIG. 1). This clone encodes a major portion of protein C, including the heavy chain coding region, termination codon, and 3' non-coding region.

The cDNA insert from λHC1375 was nick translated using α-$^{32}$P dNTP's and used to probe a human genomic library in phage λCharon 4 A (Maniatis et al., *Cell* 15:687-702, 1978) using the plaque hybridization procedure of Benton and Davis (*Science* 196:181-182, 1977) as modified by Woo (*Meth. Enzymol.* 68:381-395, 1979). Positive clones were isolated and plaque-purified (Foster et al., *Prcc. Natl. Acad. Sci. USA* 82:4673-4677, 1985, herein incorporated by reference). Phage DNA prepared from positive clones (Silhavy et al., in *Experiments with Gene Fusion*, Cold Spring Harbor Laboratory, 1984) was digested with Eco RI or Bgl II and the genomic inserts were purified and subcloned in pUC9. Restriction fragments of the genomic inserts were subcloned into M13 vectors and sequenced to confirm their identity and establish the DNA sequence of the entire gene.

The cDNA insert of pHCλ6L was nick translated and used to probe the phage λCharon 4 A library. One genomic clone was identified that hybridized to probes made from the 5' and 3' ends of the cDNA. This phage clone was digested with Eco RI, and a 4.4 kb fragment, corresponding to the 5' end of the protein C gene, was subcloned into pUC9. The resultant recombinant plasmid was designated pHCR4.4. Complete DNA sequence analysis revealed that the insert in pHCR4.4 comprised two exons of 70 and 167 base pairs separated by an intron of 1263 bp. The first exon encodes amino acids -42 to -19; the second encodes amino acids -19 to 37. Sequence analysis confirmed the DNA sequence of the entire protein C gene.

Figure 3:
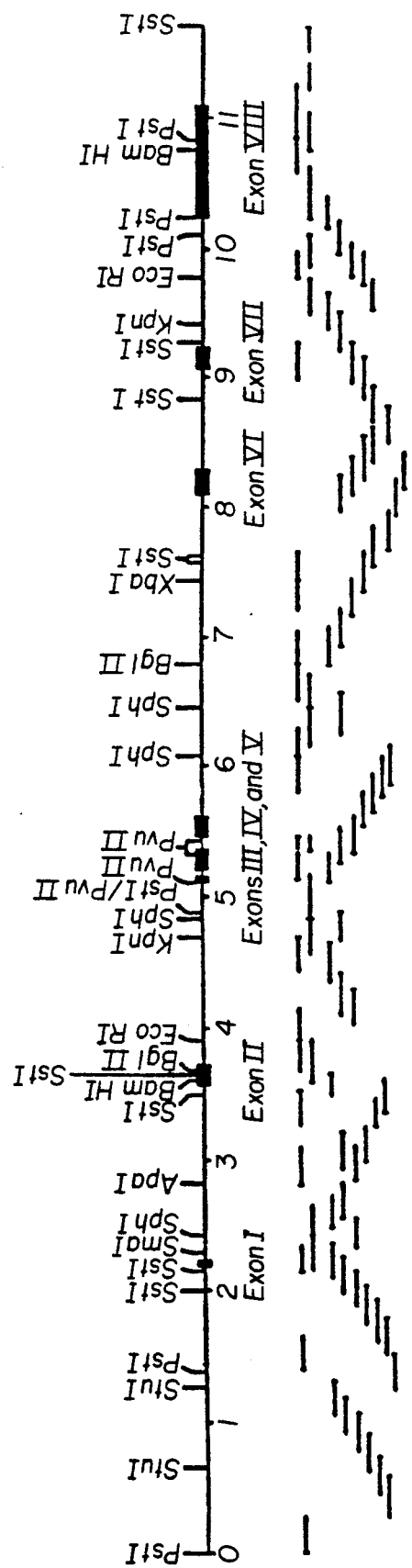
FIG. 3 illustrates a restriction enzyme map of the genomic DNA coding for human protein C. Numbers below the line indicate length in kilobases (kb).

A genomic fragment containing an exon corresponding to amino acids -42 to -19 of the pre-pro peptide (Exon 1 in FIG. 3) of protein C was isolated, nick translated, and used as a probe to screen a cDNA library constructed by the technique of Gubler and Hoffman (*Gene* 25:263-269, 1983) using mRNA from Hep G2 cells. This cell line was derived from human hepatocytes and was previously shown to synthesize protein C (Fair and Bahnak, *Blood* 64:194-204, 1984). Ten positive clones comprising cDNA inserted into the Eco RI site of phage λgt11 were isolated and screened with an oligonucleotide probe corresponding to the 5' non-coding region of the protein C gene. One clone was also positive with this probe and its entire nucleotide sequence was determined. The cDNA contained 70 bp of 5' untranslated sequence, the entire coding sequence for human pre-pro-protein C, and the entire 3' non-coding region corresponding to the second polyadenylation site (FIG. 2).

EXAMPLE 2

Construction of PC229/962

A. Construction of Vector pD3

Figure 4:
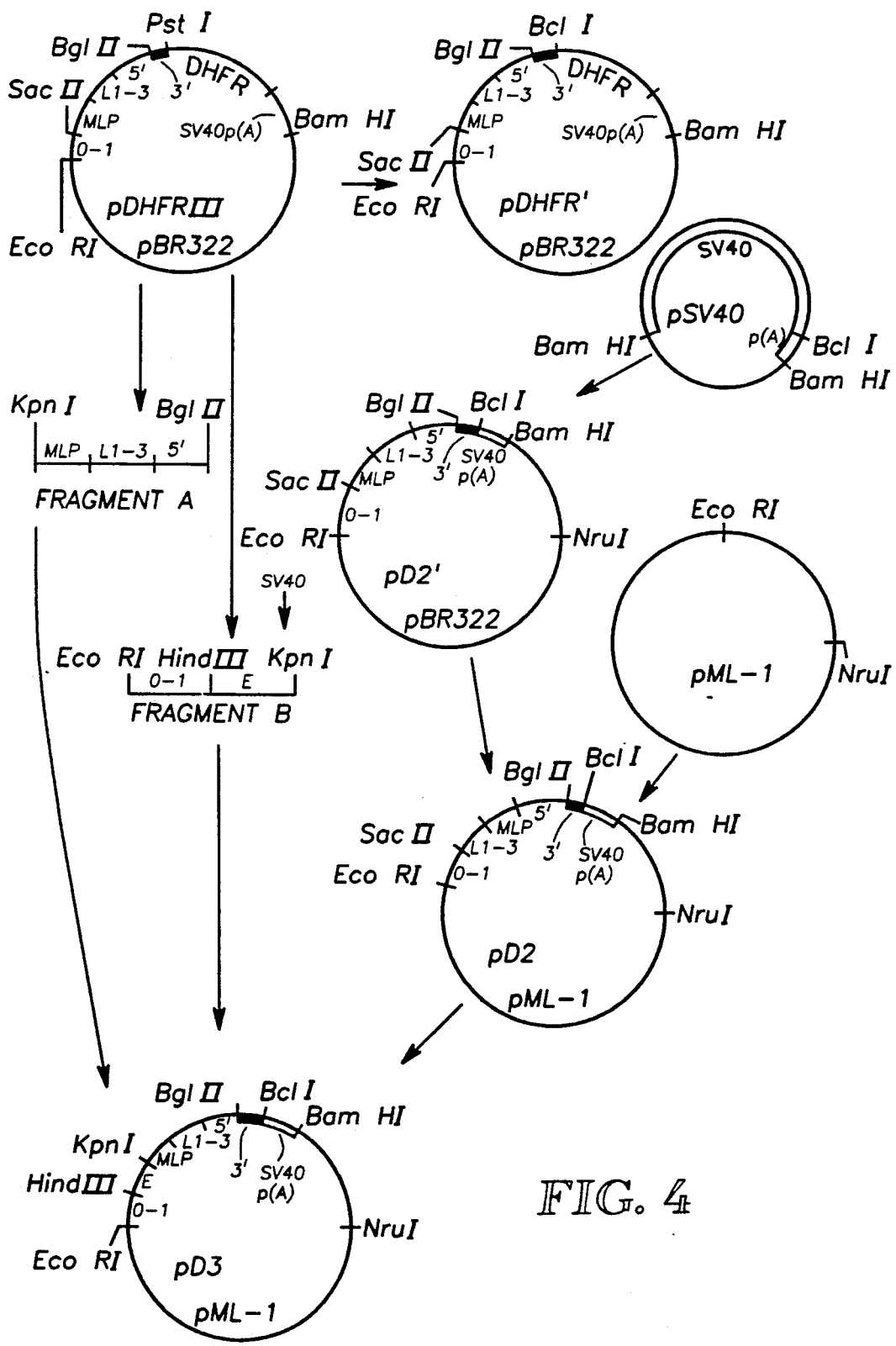
FIG. 4 illustrates the construction of the vector pD3. Symbols used are 0-1, the Adenovirus 5 0-1 map unit sequence; E, the SV40 enhancer; MLP, the Adenovirus 2 major late promoter; L1-3, the Adenovirus 2 tripartite leader; 5', 5' splice site; 3', 3' splice site; p(A), polyadenylation signal; DHFR, dihydrofolate reductase gene.

The vector pD3 was derived from pDHFRIII (Berkner and Sharp, *Nuc. Acids Res.* 13:841-857, 1985) as shown in FIG. 4. The Pst I site immediately upstream from the DHFR sequence in pDHFRIII was converted to a Bcl I site by digesting 10 μg of plasmid with 5 units of Pst I for 10 minutes at 37° C. in 100 μl restriction buffer A (10 mM Tris pH 8, 10 mM MgCl$_2$, 6 mM NaCl, 7 mM β-MSH). The DNA was phenol extracted, ethanol precipitated, and resuspended in 40 μl polymerase buffer (50 mM Tris pH 8, 7 mM MgCl$_2$, 7 mM β-MSH) containing 10 mM dCTP and 16 units T4 DNA polymerase and incubated at 12° C. for 60 minutes. Following ethanol (EtOH) precipitation, the DNA was ligated to 2.5 μg kinased Bcl I linkers in 14 μl ligase buffer (10 mM Tris pH 8, 10 mM MgCl$_2$, 1 mM DTT, 1.4 mM ATP) containing 400 units T4 polynucleotide ligase for 12 hours at 12° C. Following phenol extraction and EtOH precipitation, the DNA was resuspended in 120 μl restriction buffer B (75 mM KCl, 6 mM Tris pH 7.5, 10 mM MgCl$_2$, 1 mM DTT), digested with 80 units Bcl I for 60 minutes at 50° C., then electrophoresed through agarose. Form III plasmid DNA 910 μg) was isolated from the gel, ligated in 10 μl buffer C containing 50 units T4 polynucleotide ligase for 2 hours at 12° C., and used to transform *E. coli* HB101. Positive colonies were identified by rapid DNA preparation analysis, and plasmid DNA (designated pDHFR') prepared from positive colonies was transformed into dam *E. coli*.

Plasmid pD2' was then generated by cleaving pDHFR' (15 μg) and pSV40 (comprising Bam HI-digested SV40 DNA cloned into the Bam HI site of pML-1) (25 mg) in 100 μl restriction buffer B with 25 units Bcl I for 60 minutes at 50° C., followed by the addition of 50 units of Bam HI and additional incubation at 37° C. for 60 minutes. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 μl ligase buffer containing 100 units T4 polynucleotide ligase for 4 hours at 12° C., and the resulting construct (pD2') was used to transform *E. coli* RR1.

Plasmid pD2' was modified by deleting the "poison" sequences in the pBR322 region (Lusky and Botchan, *Nature* 293:79-81, 1981). Plasmids pD2' (6.6 μg) and pML-1 (Lusky and Botchan, ibid.) (4 μg) were incubated in 50 μl restriction buffer A with 10 units each Eco RI and Nru I for 2 hours at 37° C., followed by agarose gel electrophoresis. The 1.7 kb pD2' fragment and 1.8 kb pML-1 fragment were isolated and ligated together (50 ng each) in 20 μl ligase buffer containing 100 units T4 polynucleotide ligase for 2 hours at 12° C., followed by transformation into *E. coli* HB101. Colonies containing the desired construct (designated pD2) were identified by rapid preparation analysis. Ten μg of pD2 was then digested with 20 units each Eco RI and Bgl II in 50 μl restriction buffer A for 2 hours at 37° C. The DNA was electrophoresed through agarose, and the desired 2.8 kb fragment, comprising the pML-1, 3' splice site and poly (A) sequences, was isolated.

To generate the remaining fragments used in constructing pD3, pDHFRIII was modified to convert the Sac II (Sst II) site into either a Hind III or Kpn I site. Ten μg pDHFRIII was digested with 20 units Sst II for 2 hours at 37° C., followed by phenol extraction and ethanol precipitation. Resuspended DNA was incubated in 100 μl polymerase buffer containing 10 mM dCTP and 16 units T4 DNA polymerase for 60 minutes at 12° C., phenol extracted, dialyzed, and ethanol precipitated. DNA (5 μg) was ligated with 50 ng kinased Hind III or Kpn I linkers in 20 μl buffer C containing 400 units T4 ligase for 10 hours at 12° C., phenol extracted, and ethanol precipitated. After resuspension in 50 μl restriction buffer A, the resultant plasmids were digested with 50 units Hind III or Kpn I, as appropriate, and electrophoresed through agarose. Gel-isolated DNA (250 ng) was ligated in 30 μl ligase buffer containing 400 units T4 DNA ligase for 4 hours at 12° C. and used to transform *E. coli* RR1. The resultant plasmids were designated pDHFRIII(Hind III) and pDHFRIII(Kpn I). A 700 bp Kpn I-Bgl II fragment was then purified from pDHFRIII(Kpn I) by digestion with Bgl II and Kpn I followed by agarose gel electrophoresis.

The SV40 enhancer sequence was inserted into pDHFRIII(Hind III) as follows: 50 μg SV40 DNA was incubated in 120 μl restriction buffer A with 50 units Hind III for 2 hours at 37° C., and the SV40 Hind III fragment (5089–968 bp) was gel purified Plasmid pDHFRIII(Hind III) (10 μg) was treated with 250 ng calf intestinal phosphatase for hour at 37° C, phenol extracted and ethanol precipitated. The linearized plasmid (50 ng) was ligated with 250 ng of the SV40-Hind III fragment in 16 μl ligase buffer for 3 hours at 12° C., using 200 units T4 polynucleotide ligase, and transformed into E. coli HB101. A 700 base pair Eco RI-Kpn I fragment was then isolated from this plasmid.

For the final construction of pD3, the 700 bp Kpn I-Bgl II fragment and the 700 bp Eco RI-Kpn I fragment (50 ng each) were ligated with 10 ng of the 2.8 kb pML-1, 3′ splice site, poly(A) fragment with 200 units T4 polynucleotide ligase for 4 hours at 12° C., followed by transformation of E. coli RR1. Positive colonies were detected by rapid preparation analysis, and a large-scale preparation of pD3 (FIG. 4) was made.

B. Construction of Expression Vector p594

The expression of protein C cDNA was achieved in the vector pDX. This vector was derived from pD3 and pD3′, a vector identical to pD3 except that the SV40 polyadenylation signal (i.e., the SV40 Bam HI [2533 bp]to Bcl I [2770 bp]fragment) is in the late orientation. Thus, pD3′ contains a Bam HI site as the site of gene insertion.

Figure 5:
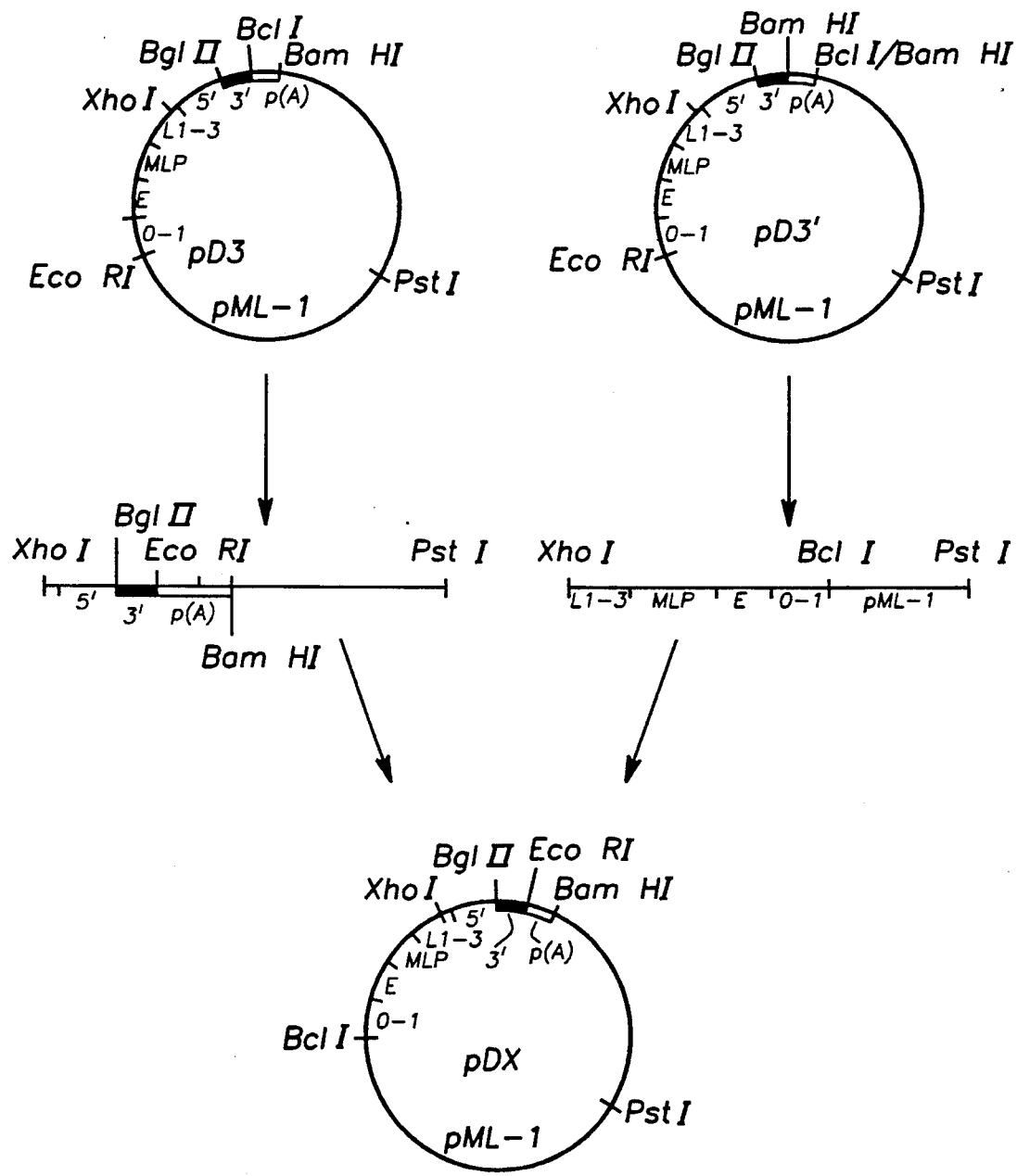
FIG. 5 illustrates the construction of the vector pDX. Symbols are used as set forth in FIG. 4.

To generate pDX, the Eco RI site in pD3′ was converted to a Bcl I site by Eco RI cleavage, incubation with S1 nuclease, and subsequent ligation with Bcl I linkers. DNA was prepared from a positively identified colony, and the 1.9 kb Xho I-Pst I fragment containing the altered restriction site was prepared via agarose gel electrophoresis. In a second modification, Bcl I-cleaved pD3 was ligated with kinased Eco RI-Bcl I adapters (constructed from oligonucleotides ZC525, 5′GGA ATT CT 3′; and ZC526, 5′GAT CAG AAT TCC 3′) in order to generate a unique Eco RI site for inserting a gene into the expression vector. A positive colony was identified by restriction endonuclease analysis, and DNA from this colony was used to isolate a 2.3 kb Xho I-Pst I fragment containing the modified restriction site. The two above-described DNA fragments were incubated together with T4 DNA ligase, transformed into E. coli HB101, and positive colonies were identified by restriction analysis. A preparation of such DNA, termed pDX (FIGS. 5), was then made. This plasmid contains a unique Eco RI site for insertion of foreign genes.

The protein C cDNA was then inserted into pDX as an Eco RI fragment. Recombinant plasmids were screened by restriction analysis to identify those having the protein C insert in the correct orientation with respect to the promoter elements, and plasmid DNA (designated pDX/PC) was prepared from a correct clone. Because the cDNA insert in pDX/PC contains an ATG codon in the 5′ non-coding region (see FIG. 2), deletion mutagenesis was performed on the cDNA prior to transfection and expression experiments. Deletion of the three base pairs was performed according to standard procedures of oligonucleotide-directed mutagenesis. The pDX-based vector containing the modified cDNA was designated p594.

C. Construction of PC229/962

To enhance the processing of single-chain protein C to the two-chain form, two additional arginine residues were introduced into the protein, resulting in a cleavage site consisting of four basic amino acids. The resultant mutant precursor of protein C, designated PC962, contains the sequence Ser-His-Leu-Arg-Arg-Lys-Arg-Asp at the cleavage site (Table 2; the amino acids that have been added to the sequence encoding wild-type (594) protein C appear in bold and spaces between amino acids are used solely for aligning the light and heavy chain sequences). Processing at the Arg-Asp bond results in a two-chain protein C molecule.

TABLE 2

Amino Acid Sequences of Cleavage-Site Mutants

594WT
149                 155                                                 170
E—K   —K—R—S—H—L—        K—R—D—T—E—D—Q—E—D—Q—V—D—P—R—L—I—D—
962
E—K—   K—R—S—H—L—R—R—K—R—D—T—E—D—Q—E—D—Q—V—D—P—R—L—I—D—

The mutant molecule was generated by altering the cloned cDNA by site-specific mutagenesis (essentially as described by Zoller and Smith, DNA 3:479–488, 1984) using the mutagenic oligonucleotide ZC962 and oligonucleotide ZC550 (Table 3). Plasmid p594 was digested with Sst I, the approximately 840 bp fragment was cloned into M13mp11, and single-stranded template DNA was isolated. Following mutagenesis, a correct clone was identified by sequencing. Replicative form DNA was isolated and digested with Sst I to isolate the mutagenized fragment. This mutagenized fragment was joined with Sst I-cut p594 in a two-part ligation. Clones having the Sst I fragment inserted in the desired orientation were identified by restriction enzyme mapping. The resulting expression vector was designated pDX/PC962 (FIG. 6).

TABLE 3

| ZC550 | 5′ TCC CAG TCA CGA CGT 3′ |
| ZC962 | 5′ ACT CAC CTG AGA AAA CGA GAC A 3′ |
| ZC1970 | 5′ GAT CTT ACC AAG T 3′ |
| ZC1971 | 5′ CAT GAC TTG GTA A 3′ |
| ZC2004 | 5′ TGC TGC TCT GTG GAG ACG GTG ACC AGT GCT TG 3′ |

A second plasmid, designated PC229/962, was constructed by inserting the PC962 cDNA into plasmid Zem229. Zem229 is a pUC18-based expression vector containing a unique Bam HI site for insertion of foreign DNA between the mouse metallothionein-I promoter and the SV40 transcription terminator. Zem229 also contains an expression unit comprising the SV40 early promoter, mouse dihydrofolate reductase gene, and SV40 terminator. An Eco RI fragment containing the PC962 cDNA from pDX/PC962 was ligated, with Eco RI-Bam HI oligonucleotide adapters, to Zem229, which had been cut with Bam HI and treated with phosphatase. The resulting vector is PC229/962, illustrated in FIG. 6.

EXAMPLE 3

Cloning of cDNA Encoding PAP-I

Figure 7:
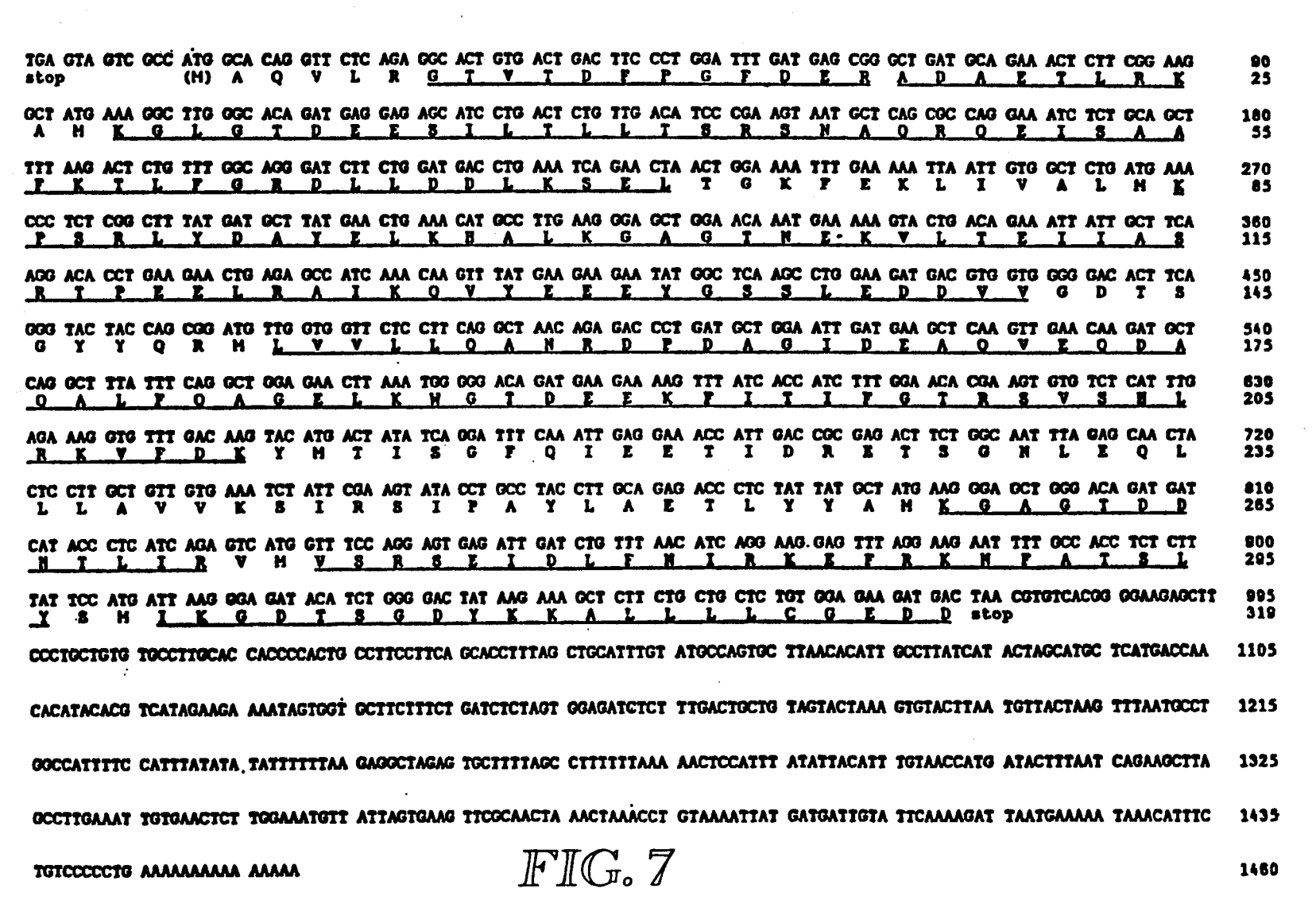

Isolation and characterization of the anticoagulant protein PAP-I is disclosed by Funakoshi et al. (*Biochemistry* 26:8087-8092, 1987). For cDNA cloning, a human placenta cDNA library (Clontech) was screened using affinity-purified antibody against PAP-I according to the methods of Young and Davis (*Proc. Natl. Acad. Sci. USA* 80:1194-1198, 1983) and Foster and Davie (*Proc. Natl. Acad. Sci. USA* 81:4766-4770, 1984). Twelve positive clones were obtained from $5 \times 10^5$ recombinants and were then plaque-purified. Sequence analysis of the largest clone (1.5 kb insert) showed that this clone contained an open reading frame sequence coding for PAP-I starting from residue 38 and extending to the 3, non-coding region containing the poly(A) tail. The original library was then re-screened using this clone as a hybridization probe. The probe was labeled by the method of Maniatis et al. (*Proc. Natl. Acad. Sci. USA* 72:1184-1188, 1975). Filters were washed with $2 \times$ SSC buffer (8.2 g of Na-citrate pH 7.0 and 17.5 g of NaCl/liter) containing 0.5% SDS at 60° C. for 1 hour. Twenty-four clones were then obtained and plaque-purified. Positive clones were subcloned into M13mp18 or M13mp19 for sequence analysis using the dideoxy-$^{35}$S method of Sanger et al. (*Proc. Natl. Acad. Sci. USA* 74:5463-5467, 1977). The largest clone (1.6 kb insert), designated λHPAP1.6, was found to encode a nearly full-length cDNA and included an initiation Met codon at the 5, end followed by the sequence encoding entire mature protein, a stop codon, and a polyadenylation signal (FIG. 7).

EXAMPLE 4

Construction of a PAP-Protein C Fusion

A PAP-Protein C fusion was constructed by using site-directed mutagenesis to fuse the PAP-I coding sequence from amino acid 1 through amino acid 326 with a protein C DNA sequence at the codon for amino acid 46. The cDNA clone λHPAP1.6 was digested with Eco RI and Bgl II to isolate the 1160 bp fragment comprising the PAP-I coding sequence. Plasmid PC229/962 was digested with Bgl II and Eco RI to isolate the 1.5 kb fragment comprising the protein C coding sequence. The two fragments were joined by ligation with Eco RI-linearized pUC9, which had been previously treated with calf alkaline phosphatase to prevent recircularization. The resulting plasmid was digested with Eco RI to isolate the 2.66 kb insert which was ligated with Eco RI-linearized, dephosphorylated M13mp18. The ligation mixture was transformed into *E. coli* JM101. Replicative form DNA was isolated from transformants and analyzed by restriction analysis to identify a clone having the insert in the antisense orientation. Single-stranded template DNA was prepared from a clone having the insert in the proper orientation. In vitro mutagenesis was carried out on the template DNA using essentially the technique described by Zoller and Smith (ibid.) and the mutagenic oligonucleotide ZC2004 (Table 3). The single-stranded DNAs from positive phage clones were sequenced using the dideoxy-sequencing method. A positive phage clone was identified, and replicative form DNA was prepared from the phage clone. The replicative form DNA was digested with Nco I and Sst I to isolate the approximately 1.7 kb fragment comprising the PAP-I-protein C coding sequences Plasmid PC229/962 was digested with Sst I and Eco RI to isolate the 1 kb fragment comprising the 3' coding sequence of protein C.

The tissue plasminogen activator (tPA) pre-pro sequence was isolated from Zem169, which was constructed as follows. A cDNA clone comprising the coding sequence for mature tPA was constructed in the inventors' laboratory using as starting material mRNA from the Bowes melanoma cell line (Rijken and Collen, *J. Biol. Chem.* 256 7035-7041, 1981). This cDNA was then used to construct the plasmid pDR1296. *E. coli* strain JM83 transformed with pDR1296 has been deposited with American Type Culture Collection under accession number 53347.

A DNA construct comprising the MT-I promoter, complete tPA coding sequence, including the natural tPA pro sequence and the human growth hormone (hGH) terminator was assembled as follows. The natural tPA pre-pro sequence was constructed from synthesized oligonucleotides and was inserted into Bam HI-digested pUC8. A Kpn I-Bam HI fragment comprising the MT-I promoter was isolated from MThGH112 (Palmiter et al., *Science* 22:809-814, 1983) and inserted into pUC18 to construct Zem93. Plasmid EV142, comprising MT-I and hGH sequences in the pBR322 derivative pBX322 (Palmiter et al., ibid.), was digested with Eco RI, and the fragment comprising the MT-I promoter and hGH terminator sequences was isolated. This fragment was cloned into Eco RI-digested pUC13 to construct plasmid Zem4. Zem93 was then linearized by digestion with Bam HI and Sal I. Zem4 was digested Bgl II and Sal I and the hGH terminator was purified. The tPA pre-pro sequence was removed from the pUC8 vector as a Sau 3 A fragment. The three DNA fragments were then joined, and a plasmid having the tPA pre-pro sequence in the correct orientation was designated Zem97. Zem97 was cut with Bgl II and the Bgl II-Bam HI tPA fragment from pDR1296 was inserted. The resultant vector was designated Zem99 (FIG. 8).

Figure 8:
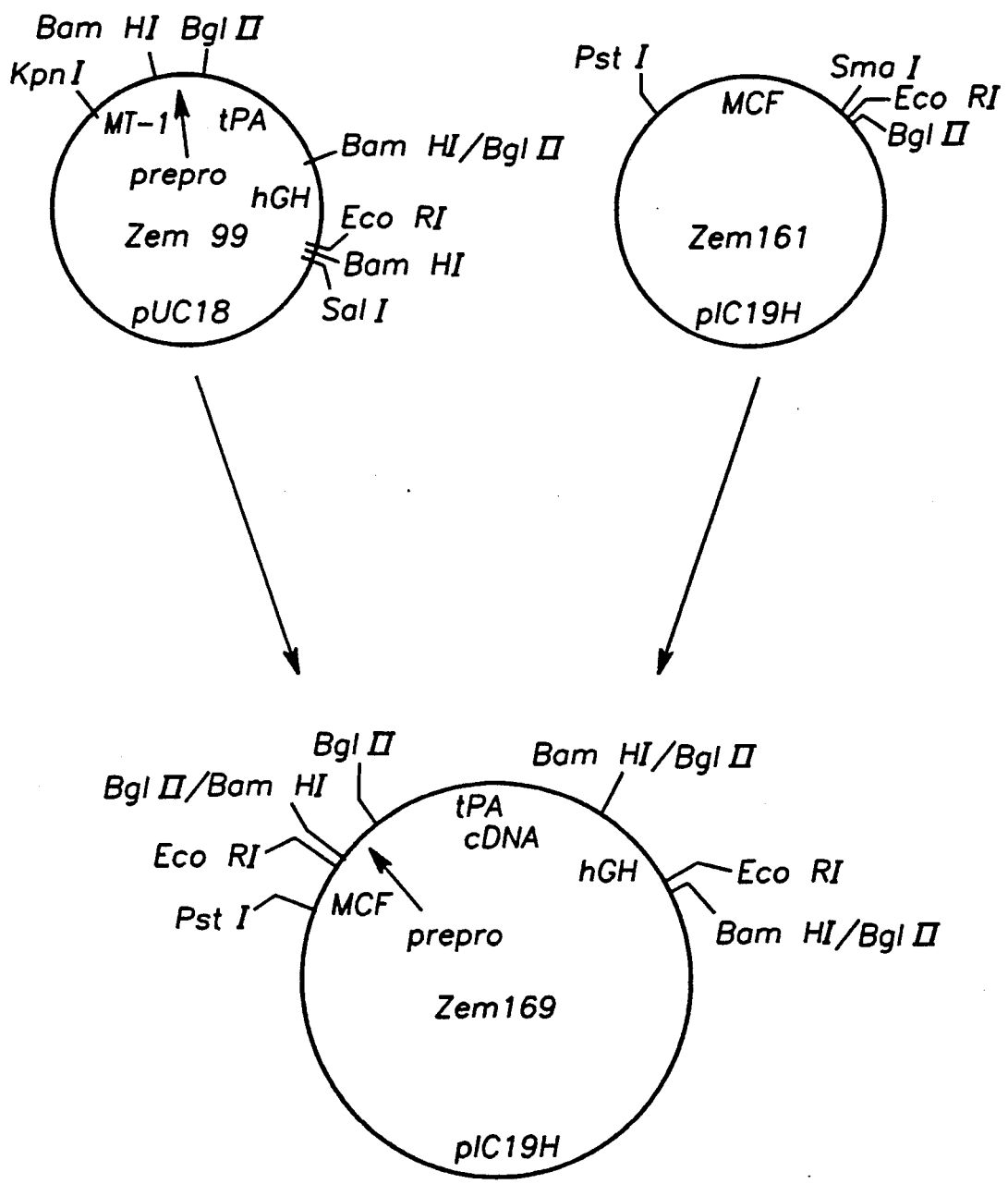
FIG. 8 illustrates the construction of plasmid Zem169. Symbols used are pre-pro, the tPA pre-pro sequence; hGH, the hGH terminator; MCF, the MCF-13 promoter.

As shown in FIG. 8, the tPA coding sequence from Zem99 was then operatively linked to the MCF-13 promoter (Yoshimura et al., *Mol. Cell. Biol.* 5:2832-2835, 1985). The MCF-13 promoter was obtained as a Pst I and Sma I fragment that was ligated with Pst I-Sma I linearized pIC19H. The resulting plasmid, designated Zem161, was linearized with Bgl II. The tPA coding sequence and human growth hormone terminator were isolated from Zem99 as a Bam HI fragment. The Bgl II linearized Zem161. and Bam HI tPA-Hgh fragment were ligated together. A plasmid containing the insert in the correct orientation relative to the promoter was designated Zem169 (FIG. 8). The tPA pre-pro sequence was isolated from Zem169 as an Eco RI-Bgl II fragment.

Oligonucleotides ZC1970 (Table 3) and ZC1971 (Table 3) were designed to form a Bgl II-Nco I adapter to operatively link the tPA pre-prosequence with the coding sequence of the PAP-I-protein C fusion. Oligonucleotides ZC1970 and ZC1971 were kinased and annealed using essentially the conditions described by Maniatis et al. (ibid.).

Figure 9:
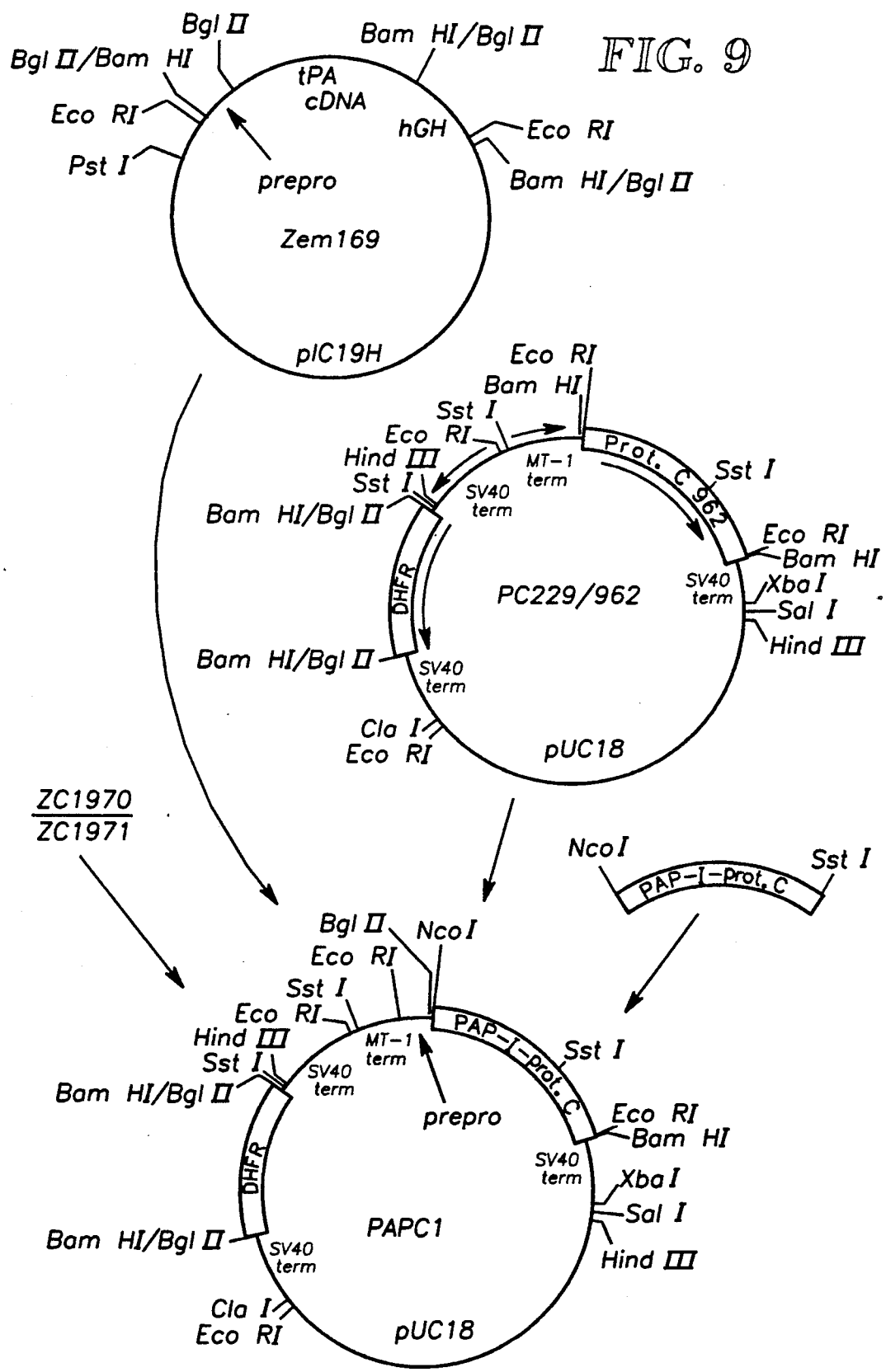
FIG. 9 illustrates the construction of a representative expression vector, PAPC, which includes a DNA sequence encoding a hybrid phospholipid-binding protein.

As shown in FIG. 9, the 1.7 kb fragment derived from the mutagenized phage clone and the 1 kb fragment derived from PC229/962 were joined with the Eco RI-Bgl II tPA pre-pro fragment and the ZC1970/ZC1971 adapter in a five-part ligation with Eco RI-linearized ZMB4. The resultant plasmid, comprising the Adenovirus major late promoter and tripartite leader, 5' and 3' splice signals, a tPA pre-pro sequence, the PAP-I-protein C fusion sequence and the hGH terminator was designated PAPCI (FIG. 9).

EXAMPLE 5

Expression of PAP-Protein C in Mammalian Cells

Plasmid PAPCI was transfected by the calcium phosphate method into BHK cells. The transfected cells were grown in Dulbecco's modified Eagle's medium (DMEM) containing 10% fetal calf seum, 1× pSN antibiotic mix (Gibco 600-5640), 2.0 mM L-glutamine and vitamin K (5 μg/ml). The cells were selected in 1000 nM methotrexate (MTX) for 10 days, and the resulting colonies were screened by the immunofilter assay (McCracken and Brown, BioTechniques, 82–87, March/April 1984). Briefly, plates were rinsed with PBS or No Serum medium (DMEM plus 1× PSN antibiotic mix, 5 μg/ml vitamin K). A Teflon® mesh (Spectrum Medical Industries, Los Angeles, Calif.) was then placed over the cells. Nitrocellulose filters were wetted with PBS or No Serum medium, as appropriate, and placed over the mesh. After a four hour incubation at 37° C., the filters were removed and placed in filter buffer (50 mM Tris pH 7.4, 5 mM EDTA, 0.05% NP-40, 150 mM NaCl, 0.25% gelatin) for 30 minutes at room temperature. The filters were incubated for 1 hour at room temperature, with shaking, in biotin-labeled sheep anti-protein C polyclonal antibody (1 μg/ml in filter buffer). Filters were then washed in the same buffer and incubated 1 hour at room temperature, with shaking, in avidin-conjugated horseradish peroxidase (Boehringer-Mannheim) (diluted 1:1000 in the filter buffer). Filters were washed in 50 mM Tris-HCl, pH 7.4, 5 mM EDTA, 1 M NaCl, 0.25% gelatin, 0.4% sarcosyl, 0.05% NP-40, then in $H_2O$. The washed filters were incubated in color reagent (60 mg HRP color development reagent [Bio-Rad], 20 ml methanol, 100 μl $H_2O_2$ in 100 ml 50 mM Tris pH 7.4, 150 mM NaCl). The reaction was stopped by transferring the filters to $H_2O$. Six of the most intensely reacting colonies were picked by cylinder cloning and were grown individually in 10 $cm^2$ plates.

Media from cylinder-cloned BHK/PAPC1 cells were assayed for PAP-I-protein C by enzyme-linked immunosorbent assay (ELISA) using a monoclonal antibody directed against the heavy chain of protein C. The monoclonal antibody to human protein C (100 μg/ml in 0.1 M $Na_2CO_3$, pH 9.6) was added to each well of 96-well microtiter plates, and the plates were incubated overnight at 4° C. The wells were washed three times with PBS (5 mM phosphate buffer, pH 7.5, 0.15 M NaCl) containing 0.05% Tween-20 to remove unbound antibody and were incubated with 100 μl of 1% bovine serum albumin, 0.05% Tween-20 in PBS at 4° C. overnight. The plates were rinsed several times with PBS, air dried, and stored at 4° C. To assay samples, 100 μl of each sample was incubated for 1 hour at 37° C. in the coated wells, and the wells were rinsed with 0.05% Tween-20 in PBS. The plates were then incubated for 1 hour at 37° C. with avidin-conjugated alkaline phosphatase in PBS containing 1% bovine serum albumin and 0.05% Tween-20. The wells were rinsed with PBS, and alkaline phosphatase activity was measured by the addition of 100 μl of phosphatase substrate (Sigma 104; 600 μg/ml in 10% diethanolamine, pH 9.8, containing 0.3 mM $MgCl_2$). The absorbance at 405 nm was read on a microtiter plate reader. Results of the assay indicated that the media contained PAP-I-protein C.

A clone of BHK/PAPC1 was grown in larger scale culture, and several hundred micrograms of the PAP-I-protein C were purified by affinity chromatography on a column prepared by coupling 7 mg of polyclonal sheep antibody against human protein C to 2 grams of CNBr-activated Sepharose 4B (Pharmacia Inc., Piscataway, N.J.). Cell culture medium was applied to the column and the column was washed with 100 ml TBS. The protein C was eluted with 6 M guanidine-HCl. Aliquots of affinity-purified protein were electrophoresed in an SDS/PAGE gel. The silver-stained gel showed three bands of 68 kD, 47 kD and 44 kD. The 47 kD and 44 kD bands were isolated for sequencing using the method described by Matsudaira (*J. Biol. Chem.* 262:10035–10038, 1987). Briefly, aliquots of the affinity-purified protein were electrophoresed in an SDS-polyacrylamide gel. The gel was soaked in transfer buffer (10 mM 3-[cyclohexylamino]-1-propanesulfonic acid, 10% methanol, pH 11.0) for five minutes. A polyvinylidene difluoride (PVDF) membrane (Millipore, Bedford, Mass.) was rinsed with 100% methanol and stored in transfer buffer. The gel was sandwiched between a rinsed PVDF membrane and sheets of 3mm CHR paper (Whatman International, Maidstone, England). The sandwich was assembled into a blotting apparatus (BioRad, Richmond, Calif.) and electro-eluted in a transfer buffer for 1 to 2 hours at 0.5 Amps. After electro-elution of the protein to the PVDF membrane, the membrane was washed with deionized water for 5 minutes. The washed membrane was stained with 0.1% Coomassie Blue R-250 in 50% methanol for five minutes. The membrane was destained in 50% methanol, 10% acetic acid for five minutes at room temperature and rinsed with deionized water for 5 minutes. The filter was air dried and stored at 4° C.

The 47kD and 44kD bands were cut out of the stained membrane, centered on the Teflon® seal, and placed in the cartridge block of the Liquid Pulse 470A sequenator (Applied Biosystems, Foster City, Calif.), where the proteins were subjected to Edman degradation. The resultant derivatives were separate by reverse phase chromatography on a C-18 column (Applied Biosystems). The sequence from the 47 kD band was homologous to PAP-I, and the sequence from the 44 kD band was homologous to the protein C-heavy chain indicating that the cells were indeed producing a PAP-I-protein C fusion.

Aliquots of the affinity-purified PAP-I-protein C were assayed for the ability to be activated to a form that shows both amidolytic and anticoagulant activities. Affinity-purified protein samples were exhaustively dialyzed against TBS, then activated by incubation at 37° C. for 1 hour with 0.1 volume of 1 unit/ml PROTAC C (American Diagnostica), a protein C activator derived from viper venom of *Agkistrodon contortix.* Amidolytic activity was measured by adding aliquots of the activation mixture to 100 μl of mM protein C substrate SPECTROZYME PCa, of the chemical formula H-D-Lys(Cho)-Pro-Arg-pNA.2AcOH, American Diagnostica) in a microtiter well and measuring the change in $A_{405}$ over time using a microtiter plate reader. Anticoagulant activity of the activated protein was assayed essentially as described by Sugo et al. (*J. Biol. Chem.* 260:10453-10457, 1985). The affinity-purified PAP-I-protein C protein was demonstrated to be fully active in both amidolytic and anticoagulant assays.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A hybrid phospholipid-binding protein comprising at least one lipocortin phospholipid-binding domain joined to a gla-domainless, vitamin K-dependent protein, wherein said hybrid phospholipid-binding protein has substantially the same biological activity as the active form of the vitamin K-dependent protein.

2. The protein of claim 1 wherein the phospholipid-binding domain is a phospholipid-binding domain of a protein selected from the group consisting of lipocortin I, lipocortin II, lipocortin III, lipocortin IV, PAP-I, lipocortin VI, and PAP-III.

3. The protein of claim 1 wherein the vitamin K-dependent protein is selected from the group consisting of prothrombin, factor VII, factor IX, factor X, protein C, protein S, bone gla protein, bone matrix protein, protein Z and pulmonary surfactant-associated proteins.

4. A hybrid phospholipid-binding protein having substantially the same biological activity as human protein C or human activated protein C said protein comprising at least one lipocortin phospholipid-binding domain joined to a gla-domainless activated protein C.

5. A hybrid phospholipid-binding protein having substantially the same biological activity as human protein C or human activated protein C, said protein comprising the amino acid sequence of FIG. 7 from amino acid 1 through amino acid 136 joined to the amino acid sequence of FIG. 2 encoding amino acid 46 through amino acid 419.

* * * * *